US010376767B1

(12) United States Patent
Shau

(10) Patent No.: US 10,376,767 B1
(45) Date of Patent: Aug. 13, 2019

(54) WEARABLE ELECTRONIC DEVICES WITH MAGNETIC SWITCHES

(71) Applicant: David Shau, Palo Alto, CA (US)

(72) Inventor: David Shau, Palo Alto, CA (US)

( * ) Notice: Subject to any disclaimer, the term of this patent is extended or adjusted under 35 U.S.C. 154(b) by 0 days.

(21) Appl. No.: 16/297,586

(22) Filed: Mar. 9, 2019

Related U.S. Application Data

(63) Continuation-in-part of application No. 16/253,230, filed on Jan. 22, 2019.

(51) Int. Cl.
*A63B 71/06* (2006.01)
*A61B 5/00* (2006.01)
*A63B 24/00* (2006.01)
*A63B 69/12* (2006.01)

(52) U.S. Cl.
CPC ........ *A63B 71/0622* (2013.01); *A61B 5/4866* (2013.01); *A63B 24/0062* (2013.01); *A63B 69/12* (2013.01); *A63B 71/0686* (2013.01); *A63B 2071/063* (2013.01); *A63B 2071/0666* (2013.01); *A63B 2220/40* (2013.01); *A63B 2220/803* (2013.01); *A63B 2220/836* (2013.01); *A63B 2225/60* (2013.01); *A63B 2244/20* (2013.01)

(58) Field of Classification Search
CPC . A63B 71/0622; A63B 69/12; A63B 71/0686; A63B 24/0062; A63B 2220/836; A63B 2071/063; A63B 2220/803; A63B 2225/60; A63B 2244/20; A63B 2071/0666; A63B 2220/40; A61B 5/4866
See application file for complete search history.

(56) References Cited

U.S. PATENT DOCUMENTS

| | | | |
|---|---|---|---|
| 3,944,345 A | 3/1976 | Decorato | |
| 4,286,340 A | 9/1981 | Lathrop | |
| 5,581,822 A | 12/1996 | Tagyo | |
| 9,734,477 B2 * | 8/2017 | Weast | A63B 24/0062 |
| 2006/0010587 A1 | 1/2006 | Yokota | |
| 2010/0030482 A1 * | 2/2010 | Li | A61B 15/1112 |
| | | | 702/19 |
| 2012/0253485 A1 * | 10/2012 | Weast | G06F 1/163 |
| | | | 700/91 |
| 2013/0226486 A1 * | 8/2013 | Henderson | H02J 7/00 |
| | | | 702/63 |

(Continued)

FOREIGN PATENT DOCUMENTS

| | | |
|---|---|---|
| CN | 201105124 | 8/2008 |
| FR | 2630653 | 11/1989 |

*Primary Examiner* — Francis C Gray

(57) ABSTRACT

Wearable electronic devices that are designed to be worn on the head of a user while the user is swimming can determine swimming strokes and swimming performances of the user accurately using motion sensors. Using a sound speaker, the wearable electronic device can play music and provide audio feedback to the swimmer. By comparing the swimming performance of the swimmer wearing the device with previously recorded swimming data, the wearable electronic device can provide audio comparison results to the swimmer while the swimmer is swimming in water. To improve water resistance, magnetic switches are utilized as selection switches. The wearable electronic device can also support similar functions for other sports and physical activities.

19 Claims, 22 Drawing Sheets

(56) References Cited

U.S. PATENT DOCUMENTS

2014/0246499 A1\* 9/2014 Proud .............. G06K 19/07762
 235/492
2017/0046108 A1\* 2/2017 Kang ................. A63B 24/0062
2019/0015041 A1\* 1/2019 Chung ................. A61B 5/0205

\* cited by examiner

FIG. 5(g)
| M1 | M2 | M3 | M4 | Actions |
|---|---|---|---|---|
| 0 | 0 | x | x | Do nothing, power down |
| 0 | 1 | 0 | 0 | Play music |
| 0 | 1 | 0 | 1 | Play music while swimming |
| 0 | 1 | 1 | 0 | Synchronize music tempo to swimming pace |
| 0 | 1 | 1 | 1 | Adjust volume according to swimming speed |
| 1 | 0 | 0 | 0 | Lap count |
| 1 | 0 | 0 | 1 | Lap count + lap time |
| 1 | 0 | 1 | 0 | Lap count + lap time + stroke count |
| 1 | 0 | 1 | 1 | Report Calories burned |
| 1 | 1 | 0 | 0 | Lap count + music |
| 1 | 1 | 0 | 1 | Lap count + lap time + music |
| 1 | 1 | 1 | 0 | Lap count + lap time + paced music |
| 1 | 1 | 1 | 1 | Store data into memory |
FIG. 5(h)
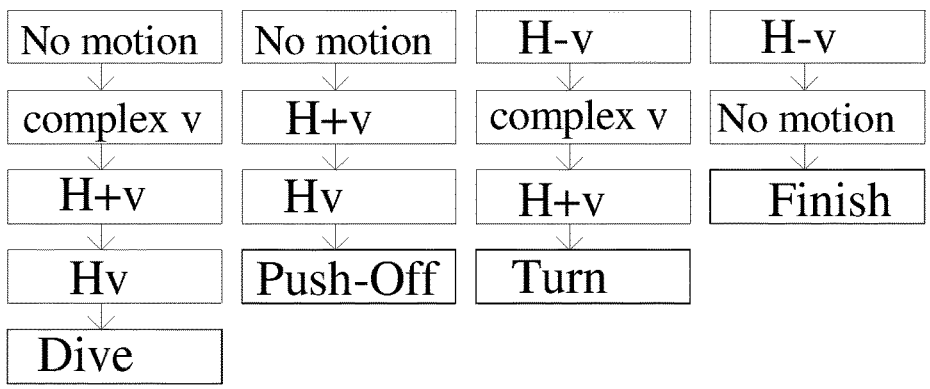
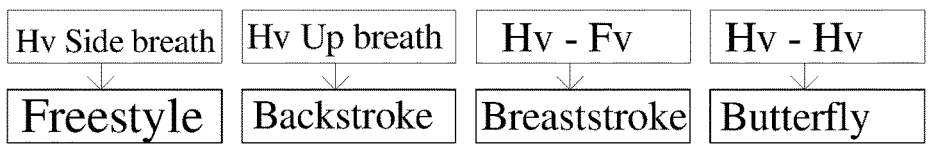

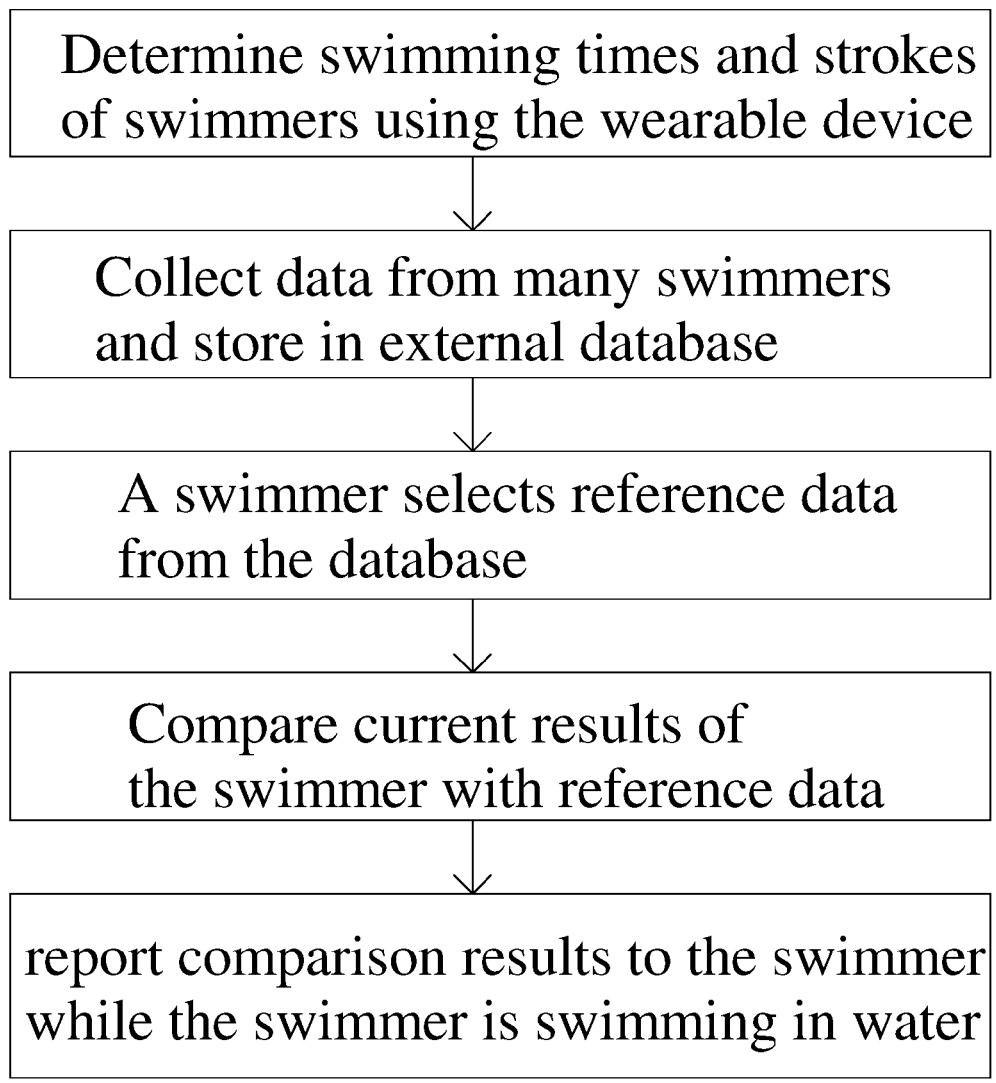

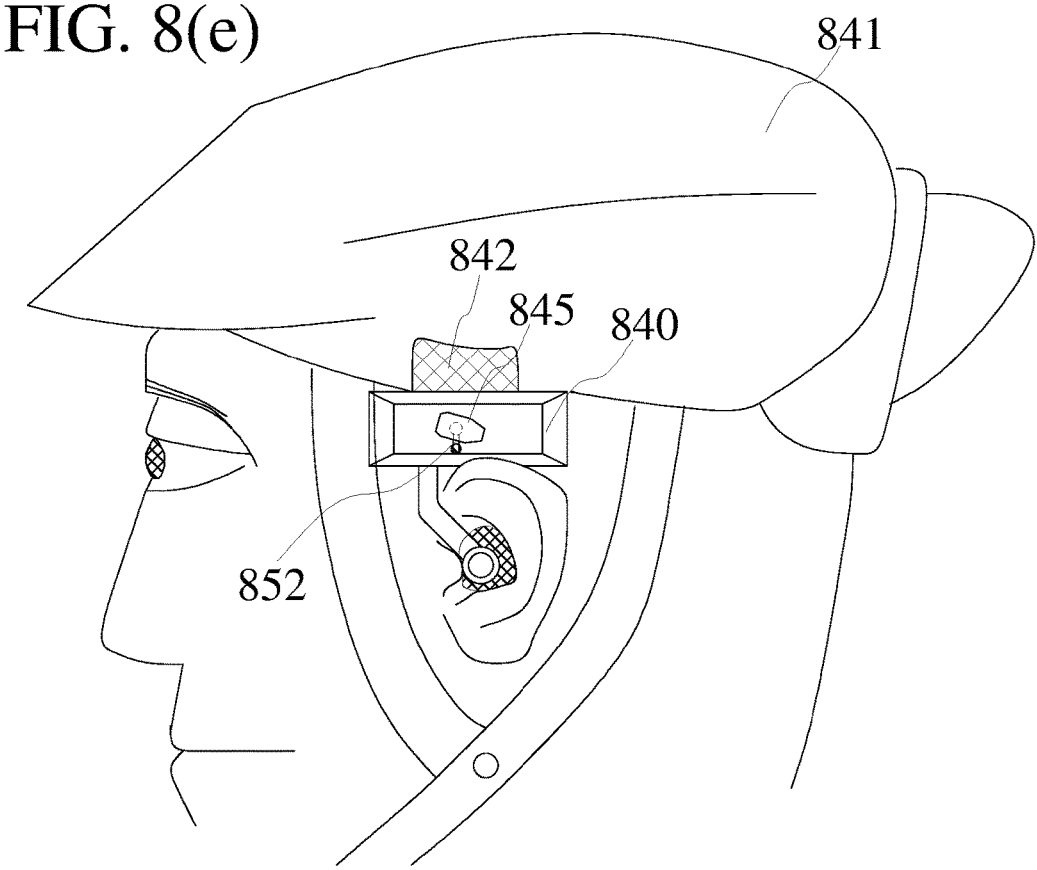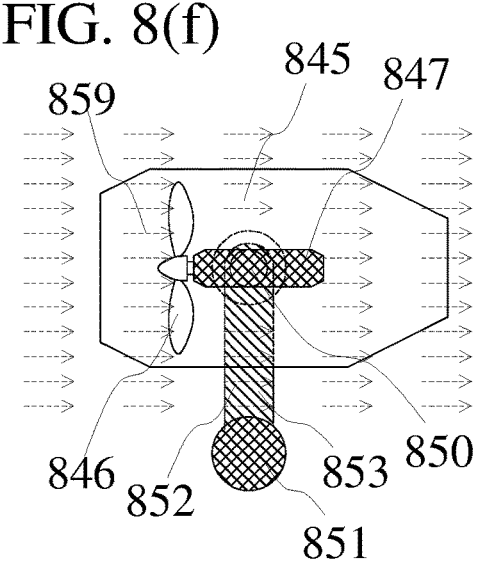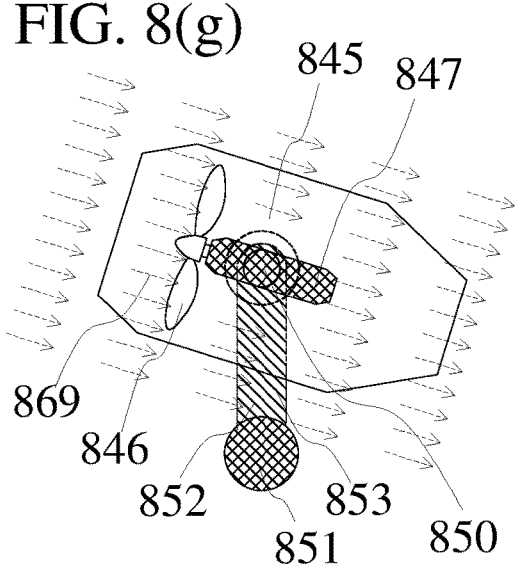

WEARABLE ELECTRONIC DEVICES WITH MAGNETIC SWITCHES

This application is a continuation-in-part application of the previous patent application with a Ser. No. 16/253,230, with a title "Wearable Electronic Devices with Swimming Performance Comparison Capabilities", filed by David Shau on Jan. 22, 2019.

BACKGROUND OF THE INVENTION

The present invention relates to wearable electronic devices for swimmers that provide swimming performance comparisons while the swimmer wearing the wearable electronic device is swimming in water.

Swimming is a sport that keeps people in great shape. Swimming exercises most of the body's muscles, and swimming can even save one's life. For most of competitive sports, it is almost guaranteed that people will eventually get hurt by sport injuries. In comparison, swimming is a sport that rarely causes serious injury. However, like me, most swimmers have bumped their head at the end of the pool while swimming backstroke. While at full sprinting speed, this type of injury may even result in minor concussions, and is also quite painful. It is desirable to design swimming goggles that allow swimmers to see the end of the pool without moving their head while swimming in backstroke. Also, backstroke swimmers often swim in a curvy zigzag path in their lane instead of a simple direct straight line. If the swimmer swims in a zigzag path, then the distance that they swim will be longer, and it also makes them look bad. It is desirable for a swimmer to see the sights behind them while swimming backstroke, so that they may line up their position, thus allowing the swimmer to swim in a straight line. It is also desirable to have swimming goggles that can help swimmers maintain proper head position while swimming backstroke.

Decorato in U.S. Pat. No. 3,944,345 disclosed a swimming goggle equipped with special lens that attaches onto the front of the eye sockets, increasing the user's lateral vision. It, however, does not enable the ability to see behind his or herself, and does not provide wide enough visual range to support backstroke.

Lathrop in U.S. Pat. No. 4,286,340 disclosed a pair of comfortable competition goggles with anti fog washing, watertight fits that enhance the eyesight, and improved forward vision that allows the user to see the wall without lifting their head while swimming the crawl, breast, and butterfly strokes. The swimming goggles, however, does not improve backwards vision, and cannot benefit the ability to see the end of the pool without moving their head while swimming in backstroke.

Tagyo in U.S. Pat. No. 5,581,822 disclosed an attractively shaped pair of goggles that provide watertight vision, and allow the user to swim faster due to its smooth single large lens. It, however, does not provide the ability to see the wall while swimming backstroke.

Yokota in US Patent Application No. 20060010587 disclosed a pair of goggles that use a contact section that attaches to the area around the eye in the eye socket, therefore, improving the user's field vision. The goggles also prevent light refraction that may cause discomfort to the owner. These goggles may enhance the peripheral vision while swimming backstroke, but it does not give a clear vision of the wall; the swimmers still need to change their normal head positions to see the wall. It also does not use a light reflector.

Desbordes in French patent number FR 2630653 disclosed a swimming goggle that has a backstroke viewing window and a light reflector. The light reflector does not switch position with respect to the front viewing window, and it does not change position depending on the body motions of the swimmer.

Huang in Chinese patent number CN201105124 disclosed a swimming goggle that has a backstroke viewing window and a light reflector. Huang apparatus provides visibility to overhead direction when the swimmer is in position for backstroke, freestyle, and diving in order to avoid colliding with other swimmers in a crowed swimming pool. Huang's apparatus does not address the needs to view different parts of the swimming pool while the swimmer is swimming backstroke versus freestyle.

None of the above prior art swimming goggles comprise electric control mechanisms.

Li in US publication number 2010/0030482 disclosed devices that monitor the body orientation of a swimmer, and provide real time comparisons between the current performance of the swimmer and previously achieved performances of the same swimmer. However, Li's device does not measure the head orientation of a swimmer. Head orientation is significantly different from body orientation because the accelerations at the head of a swimmer are significantly different from the accelerations at the body of a swimmer. This is because head motions are very different than body motions when swimming, an idea that has been proven by experimental results. Furthermore, Li does not compare the results of different swimmers, does not adjust the reference data for different swimming conditions, and does not disclose comparisons with universally accepted swimming time standards.

Gear worn by swimmers must be able to withstand strong forces in the water when swimmers are diving, turning, or swimming various strokes at high speeds. The previous application with the Ser. No. 16/253,230 disclosed wearable electronic devices that provide feedback using voice, music, or by adjusting goggle components, and provides additional feedback to the user by comparing the user's current swimming performance with recorded swimming performances, or swimming performances of another swimmer. The previous application also suggested the use of contactless switches to improve water resistance. This patent application discloses further details of such contactless switches and their applications.

SUMMARY OF THE PREFERRED EMBODIMENTS

A primary objective of the preferred embodiments is, therefore, to provide swimming goggles that allow the user to see behind him or her without changing their normal head position while swimming backstroke. This will reduce the chance of injury, since they can now see where the wall is. Another objective is to prevent the swimmer from swimming in a zigzag manner when they swim across the pool in their lane. This will allow the swimmer to go faster, and prevent the user from crashing into the lane lines. Another primary objective is to provide sophisticated motion related information to a swimmer while the swimmer is swimming. Another objective is to provide an electronic controller that can be detached from a swimming goggle so that the same electronic controller can be utilized on multiple swimming goggles. Another primary objective is to provide accurate measurements of the speed of the users. Another objective is to re-charge the battery while the users are swimming or exercising. These and other objectives are assisted by providing swimming goggles with backstroke viewing windows at the eye sockets, using motion sensors such as accelerometers or flow meters, and using integrated circuits attached to the athletic headgear. Another objective is to provide feedback to the user by comparing his or her swimming performances to that of other swimmers, or to previous swimming performances of the same user. Another objective is to provide feedback to the user by comparing his or her athletic performances to that of other athletes. Another primary objective is to improve the water resistances of wearable electronic devices using contactless switches.

While the novel features of the invention are set forth with particularly in the appended claims, the invention, both as to organization and content, will be better understood and appreciated, along with other objects and features thereof, from the following detailed description taken in conjunction with the drawings.

BRIEF DESCRIPTION OF THE DRAWINGS

FIG. 5(g) shows a table that lists exemplary modes supported by the electric controller in FIG. 5(c);

FIG. 5(h) is a symbolic block diagram illustrating how procedures are executed to determine the actions of a swimmer wearing a swimming goggle equipped with flow meters;

FIG. 5(i) is an exemplary flowchart for swimming data comparison procedures;

FIGS. 6(d, e) are cross section diagrams showing exemplary structures when the wearable electronic device in FIG. 6(a-c) is using a magnetic switch;

DETAILED DESCRIPTION OF THE PREFERRED EMBODIMENTS

Figure 1A:
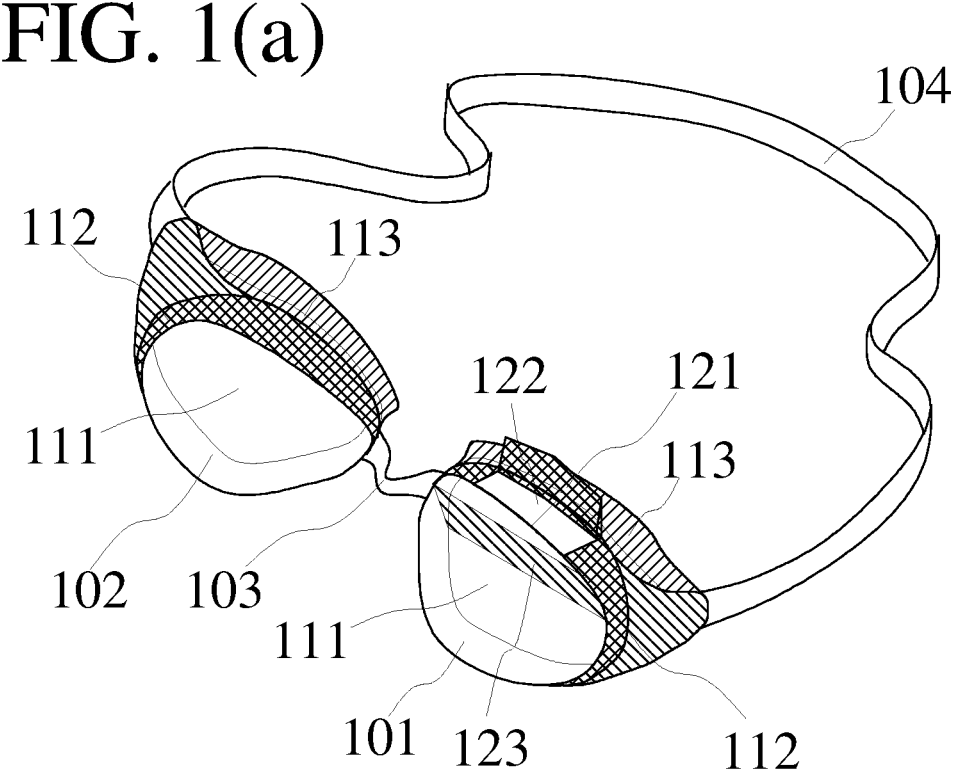
FIG. 1(a) shows one example of the swimming goggles of the present invention that has a backstroke viewing window on one eye socket.
Figure 1B:
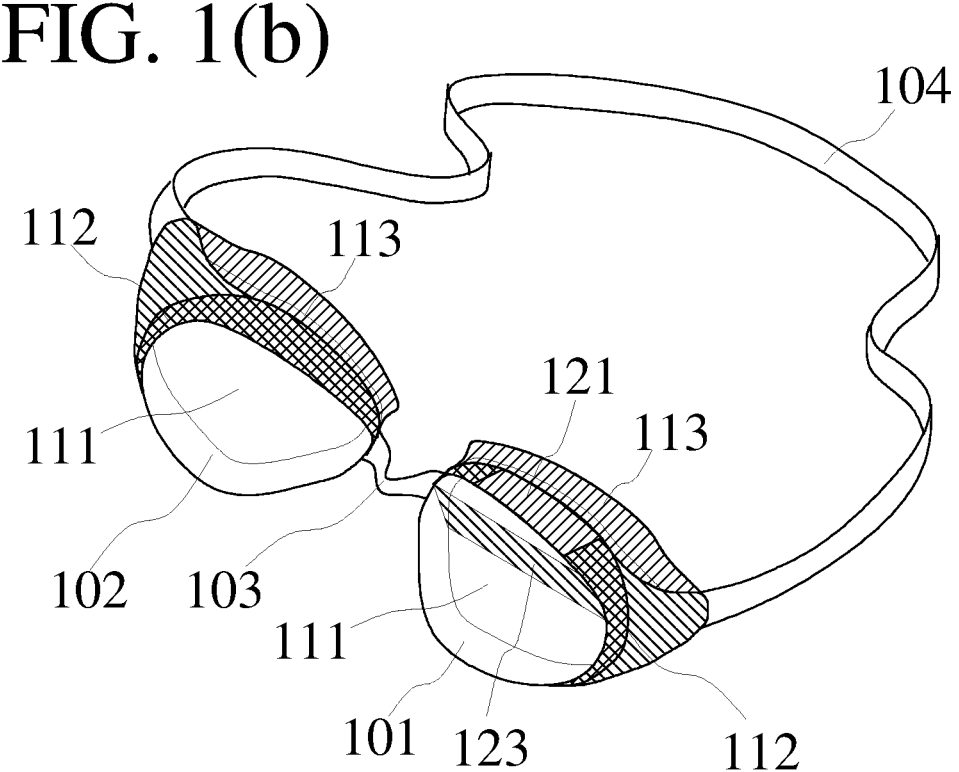
FIG. 1(b) shows the swimming goggle in FIG. 1(a) while the light blocking cover of the backstroke viewing window is closed.

FIGS. 1(a-d) show examples of the goggles of the present invention. The goggles in these examples comprise two eye sockets (101, 102) connected by a nosepiece (103) and a head strap (104). Each eye socket (101, 102) has a forward viewing window (111) that is mounted on a suction socket (113). Typically, the forward viewing window (111) is made of transparent plastic plate, and the suction socket (113) is made of rubber or plastic. The suction socket (113) sticks onto swimmer's eyes, creating a water tight seal while providing a space between the eye and the forward viewing window (113), allowing clear under-water vision. These structures are similar to those used in conventional swimming goggles. In addition, the examples in FIGS. 1(a-d) contain structures that are designed to allow the swimmer to see the end of the pool without moving their head while swimming in backstroke. For example, FIGS. 1(a, b) illustrate a goggle that has a backstroke viewing window (122) opened at the upper side (112) of the eye socket. A backstroke viewing window, by definition, is a transparent window on the eye socket of a swimming goggle that faces upward direction while the swimmer wearing the goggle is standing upright so that it faces the end of swimming pool when the swimmer is in normal head position while swimming backstroke. A backstroke viewing window is typically nearly vertical to the front viewing window. In this example, the backstroke viewing window (122) is made of transparent plastic. To prevent unwanted peripheral lights, the backstroke viewing window (122) can be covered with a light blocking cover (121). FIG. 1(a) illustrates the situation when the light blocking cover (121) of the backstroke viewing window (122) is opened, and FIG. 1(b) illustrates the situation when the light blocking cover (121) is closed. In this example, a light reflector (123) is placed inside the eye socket (101), as illustrated in FIGS. 1(a, b). In this example, the light reflector (123) is a transparent plastic plate supporting the functions of a half-mirror. A half-mirror, by definition, is a light reflector that is partially transparent and partially reflecting. In this example, the index of reflection of the light reflector (123) is adjusted in such way that the reflected view is more dominating than the transparent view. When the light blocking cover (121) of the backstroke viewing window (122) is opened, as shown in FIG. 1(a), the light that travels through the backstroke viewing window (122) is reflected by the light reflector (123), allowing the swimmer to see the end of the pool without moving head while swimming in backstroke. When the light blocking cover (121) of the backstroke viewing window (122) is closed, as shown in FIG. 1(b), almost no light would come from the upward direction so that the swimmer would see views at the front direction through the half-mirror light reflector (123).

While the preferred embodiments have been illustrated and described herein, other modifications and changes will be evident to those skilled in the art. For example, the light reflector (123) can be a mirror instead of a half-mirror. For another example, FIG. 1(c) shows another goggle that has a backstroke viewing window (124) without a light blocking cover. This goggle can be manufactured at lower cost, but users may see unwanted lights from upward direction. Another example in FIG. 1(d) shows a goggle with backstroke viewing windows (124, 125) and light reflectors (123, 126) in both eye sockets (101, 102). This goggle allows better upward vision because both eyes are now able to see the same reflection, but front view will be less clear. It is to be understood that there are many other possible modifications and implementations so that the scope of the invention is not limited by the specific embodiments discussed herein.

Figure 2A:
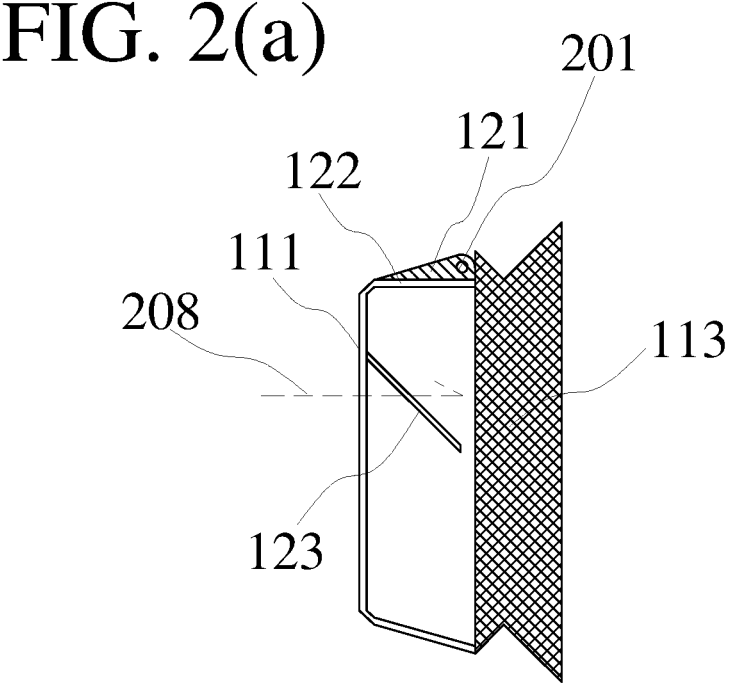
FIG. 2(a, b) are cross-section views of an eye socket that can automatically switch the position of the light blocking cover of the backstroke viewing window.
Figure 2B:
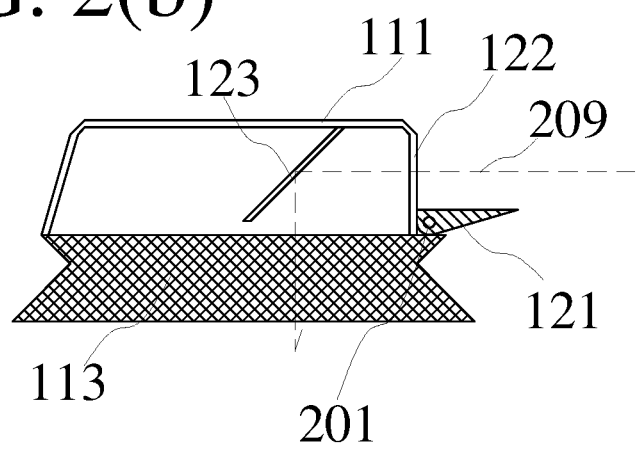
Figure 3A:
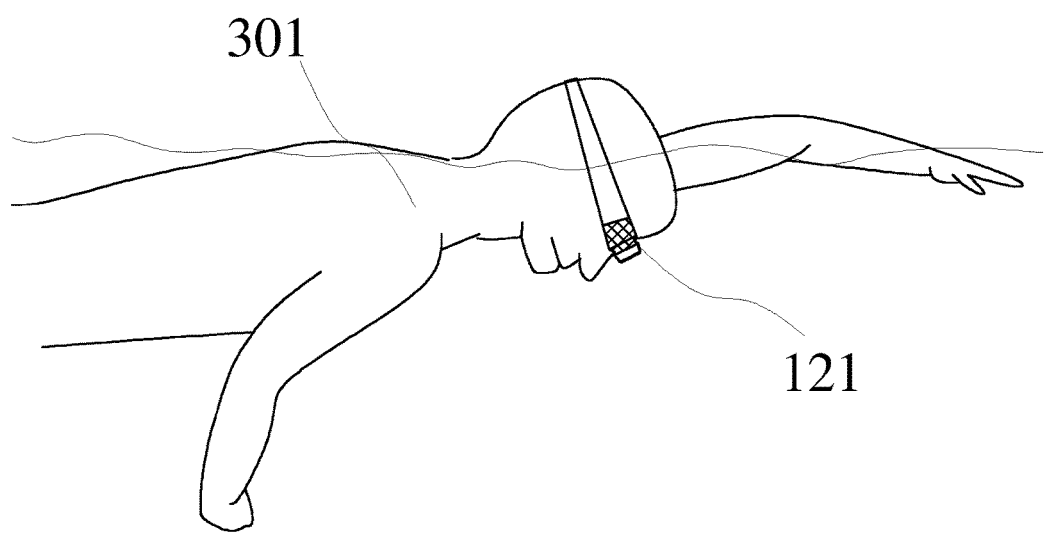
FIG. 3(a) shows a simplified view of a user who is swimming freestyle on his front.
Figure 3B:
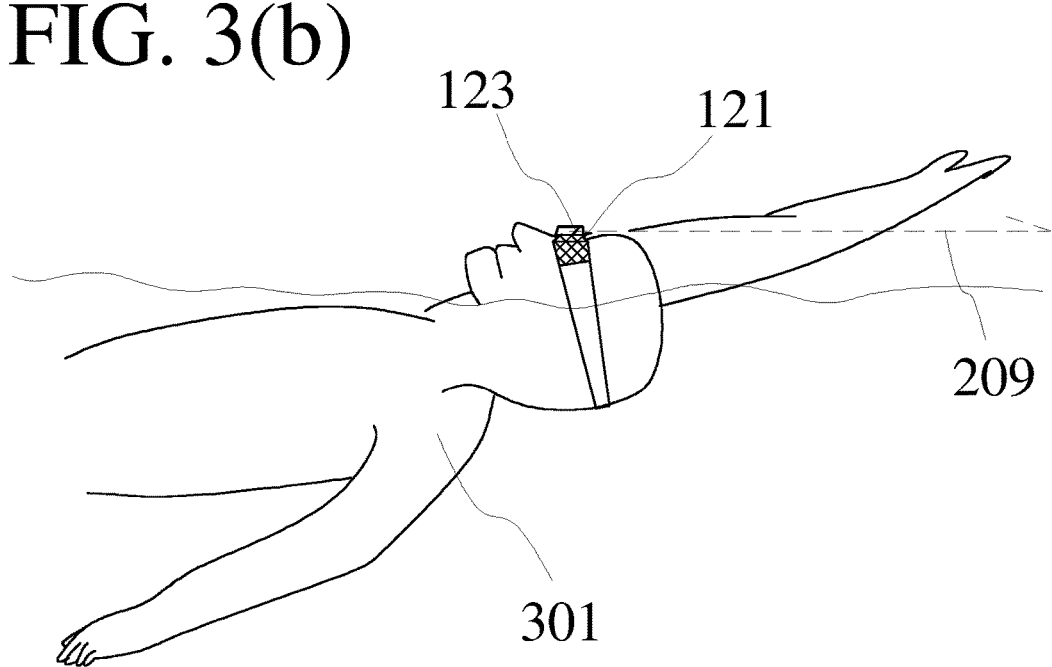
FIG. 3(b) shows a simplified view of a user who is swimming backstroke on his back.

The light blocking cover (121) of the backstroke viewing window (122) shown in FIGS. 1(a, b) may be opened or closed manually. A swimmer can open the light blocking cover while swimming backstroke, and close it while swimming other strokes. While swimming melody, a swimmer needs to swim backstroke and other strokes. Flipping the light block cover while swimming can be troublesome. It is desirable to open or close the light blocking cover (121) automatically according to the stroke the swimmer is swimming. FIGS. 2(a-b) show cross-section views of an eye socket that can open or close the light blocking cover (121) automatically. In this example, the light blocking cover (121) is designed to rotate around a rotation axis (201). When the socket is at a position as illustrated in FIG. 2(a), the light blocking cover (121) is closed due to gravity. Under this situation, the light (208) passes directly through the half mirror (123) allowing the user to see what they would normally see while facing forward. Due to gravity, the light blocking cover (121) is also closed when the eye socket is facing downward. FIG. 3(a) illustrates the situation when a swimmer (301) wearing the goggle is swimming freestyle. Under this situation, the light blocking cover (121) of the backstroke viewing window is closed so that the swimming goggle functions as a conventional goggle. While swimming backstroke, the eye socket would face upward as illustrated by FIG. 3(b) and by the cross-section diagram in FIG. 2(b). At this position, the light blocking cover (121) would rotate backward along the rotation axis (201) by gravity, opening the backstroke viewing window (122) as illustrated in FIG. 2(b). The light (209) through the opened window (122) is reflected by the light reflector (123), allowing the swimmer (301) to see the end of the pool without moving his head while swimming in backstroke.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, the light reflector also can be automatically switched into position as shown by the cross-section diagrams in FIGS. 4(a-b).

Figure 4A:
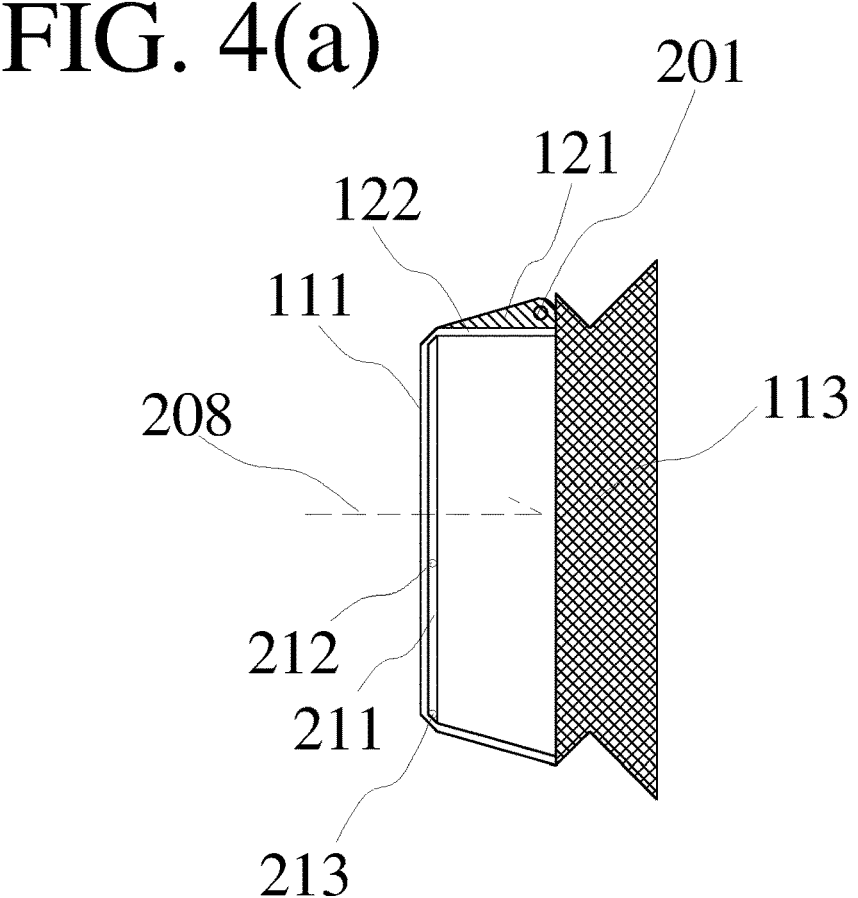
FIG. 4(a, b) are cross-section views of an eye socket that can automatically switch the positions of the light blocking cover and the light reflector.
Figure 4B:
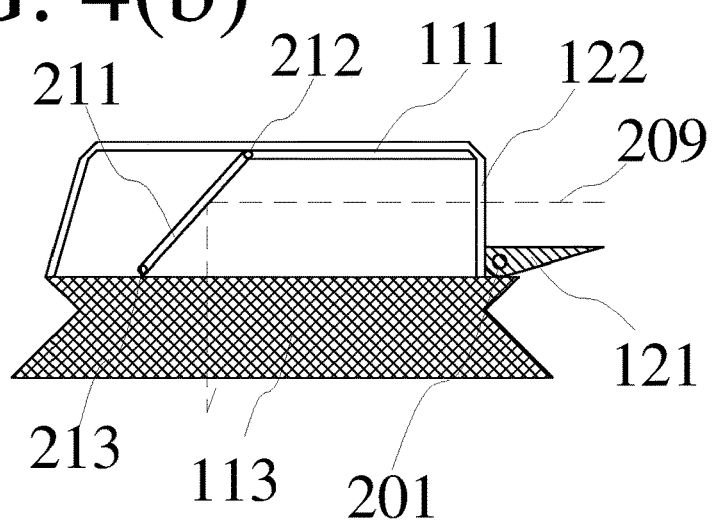

The eye socket shown in FIGS. 4(a-b) is similar to the eye socket shown in FIGS. 2(a, b) except that it has a light reflector (211) that can rotate against a rotation axis (212). A weight (213) is placed near the end of the light reflector (211) so that its position can be switched by gravity. When the socket is at a position illustrated in FIG. 4(a), the light reflector (211) is pulled by gravity to be in contact with the front viewing window (111) and functions as part of the front viewing window. Under this situation, the eye socket behaves as a conventional eye socket. Due to gravity, the position of this light reflector (211) would remain the same while the swimmer is swimming freestyle, breast, or butterfly strokes. While swimming backstroke, the eye socket would face upward, and the light reflector (211) would fall down due to gravity, as shown in FIG. 4(b). The light (209) through the opened backstroke viewing window (122) is reflected by the light reflector (211), allowing the swimmer to see the end of the pool without moving their head while swimming in backstroke.

The preferred embodiments of the present invention provide swimming goggles that allow the user to see the end of swimming pool without changing normal head position while swimming backstroke. The chance of injury is reduced because backstroke swimmers can now see where the wall is. The backstroke swimmer also can adjust swimming direction by vision to swim in straight line to achieve better time. These and other objectives are achieved by opening backstroke viewing windows at the eye sockets of swimming goggles. A light blocking cover can be used to prevent unwanted light going through the backstroke viewing window. The light blocking cover can be operated manually or automatically. A light reflector is typically used with the backstroke viewing window. This light reflector can be a half mirror or a full mirror. The light reflector also can be designed to change position automatically according the stroke the swimmer is swimming.

While the preferred embodiments have been illustrated and described herein, other modifications and changes will be evident to those skilled in the art. It is to be understood that there are many other possible modifications and implementations so that the scope of the invention is not limited by the specific embodiments discussed herein. While the examples in FIG. 4(a, b) automatically switch the position of the light blocking cover and the light reflector by gravity, we can also use the buoyant force of water, the body motions of the swimmer, and other methods to switch the positions of the light blocking cover or the light reflector. FIGS. 5(a-g) show an exemplary swimming goggle that switches the position of the light blocking cover and the position of the light reflector by an electric controller.

Figure 1C:
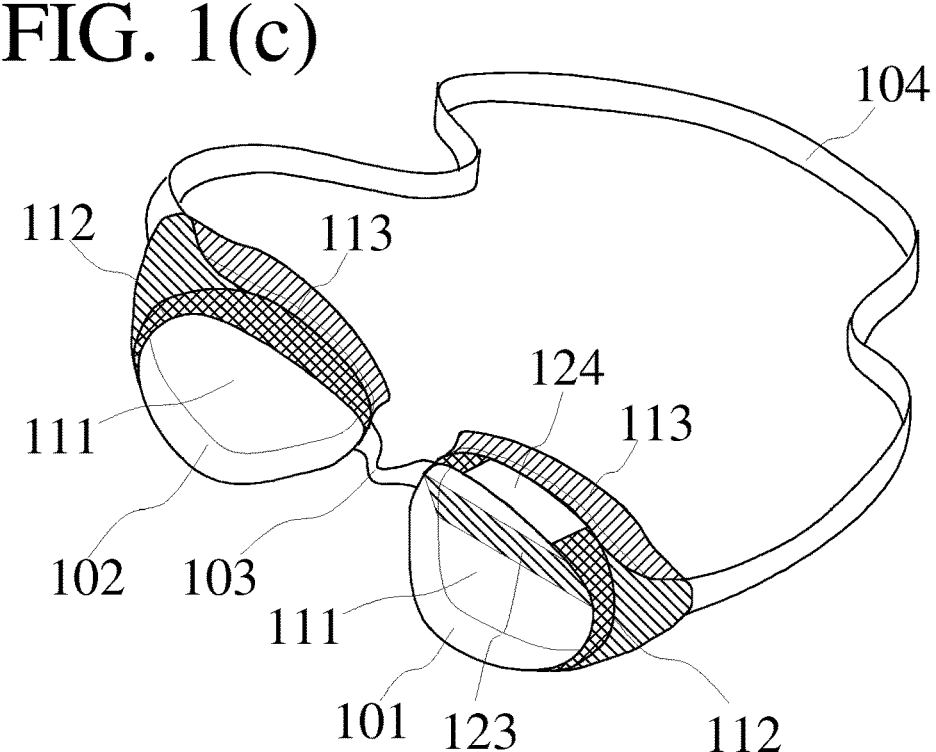
FIG. 1(c) shows a goggle without a light blocking cover on the backstroke viewing window.
Figure 1D:
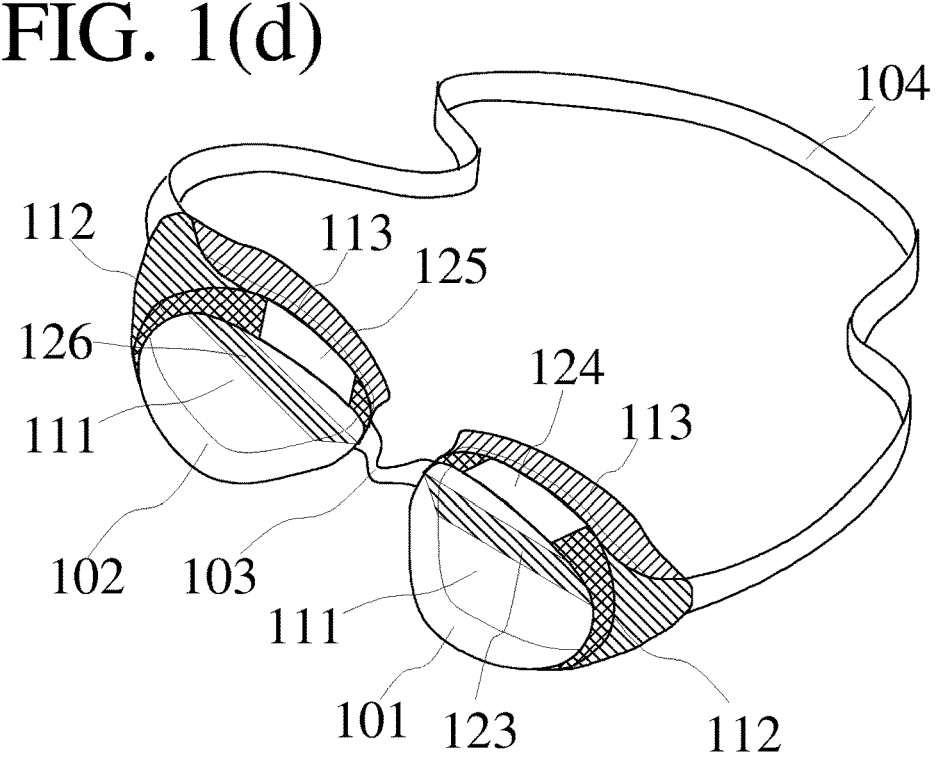
FIG. 1 (d) shows a goggle with backstroke viewing windows on both eye sockets.
Figure 5A:
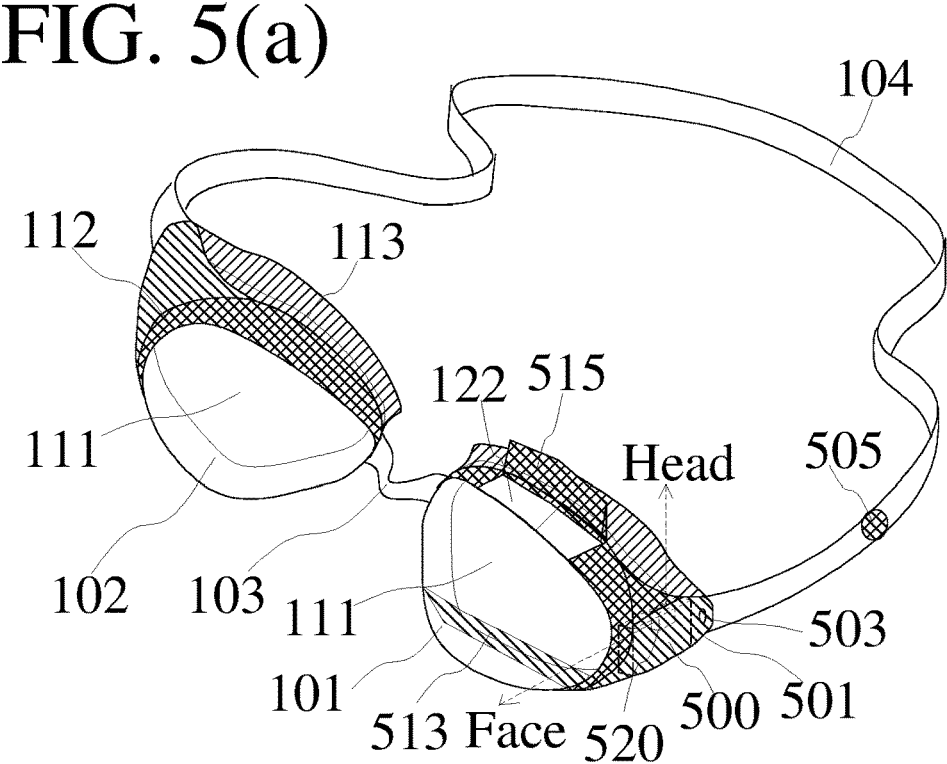
FIG. 5(a) shows a swimming goggle that has an electric controller (500) and an electric sound speaker (505)

FIG. 5(a) shows a swimming goggle that has the same structures as those of the swimming goggle in FIG. 1(a) except that the swimming goggle in FIG. 5(a) has an electric sound speaker (505) attached to its head strap (104), and an electric controller (500). This electric controller (500) is able to control the position of a light reflector (513) and the position of a light blocking cover (515). The electric controller (500) is covered by a watertight cover (501) when the goggle is used in water. A button (503) on the watertight cover (501) allows the user to open the cover in order to adjust operation modes of the electric controller (500). A motion sensor (520) is placed inside of the electric controller (500). This motion sensor (520) is attached to the swimming goggle at a fixed position with respect to the forward viewing window (111), and outputs electric signals that are related to the motions of the swimmer wearing the swimming goggle. One example of a motion sensor that can be used for this purpose is the LIS332AR motion sensor made by STMicroelectronics. LIS332AR is an accelerometer that measures a three-dimensional acceleration vector, and outputs three voltages, which are proportional to the three components of the acceleration vector along its x, y, and z directions. For the example in FIGS. 5(a-g), the motion sensor (520) can be an LIS332AR accelerometer that is placed at a position where its x axis is pointing towards the viewing direction through the forward viewing window (111), as illustrated by the dashed lined arrows in FIGS. 5(a, b). This direction will be called the "Face direction" in the following discussions. The y axis of the motion sensor (520) is pointing towards the viewing direction through the back stroke viewing window (122), as illustrated by the dashed lined arrows in FIGS. 5(a, b). This direction will be called the "Head direction" in the following discussions. For this example, the electric sound speaker (505) is attached to the head strap (104) of the swimming goggle in FIG. 5(a). The electric sound speaker (505) also can be an earbud or a speaker in other shapes.

Figure 5B:
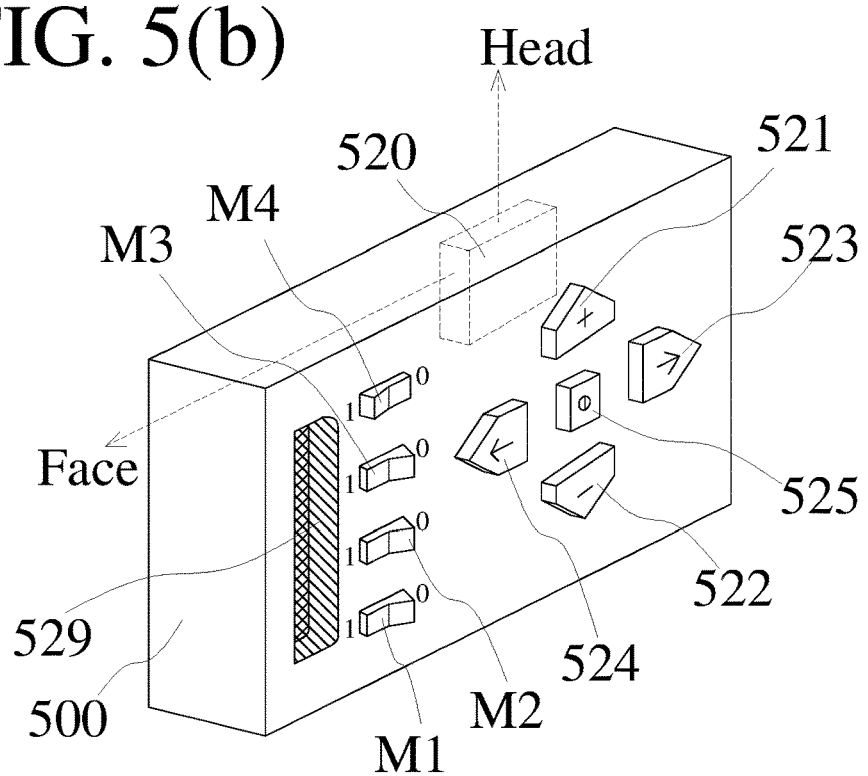
FIG. 5(b) shows a close up of the electric controller in FIG. 5(a)
Figure 5C:
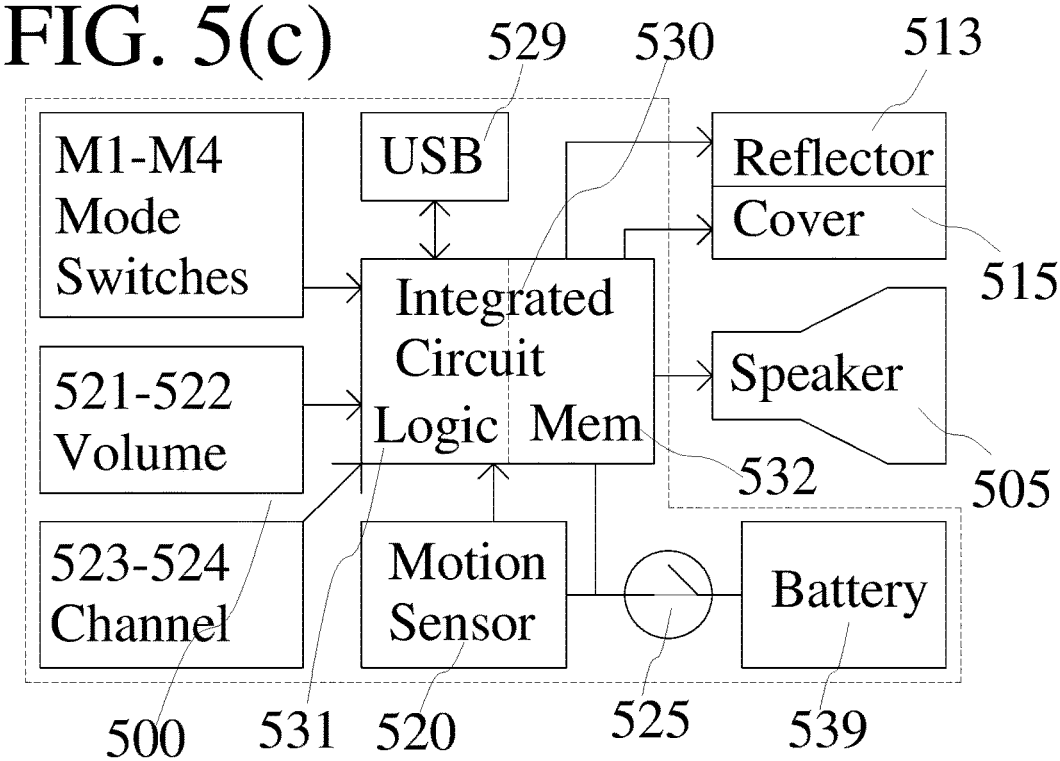
FIG. 5(c) is a symbolic block diagram for the electric controller and output devices in FIG. 5(b)

A user can open the watertight cover (501) on the swimming goggle to reach the front panel of the electric controller (500). As shown in FIG. 5(b), the front panel of the electric controller (500) comprises a USB interface socket (529), four mode-select switches (M1-M4), two volume control switches (521-522), two channel-select switches (523, 524), and a power switch (525). All the other electric components of the electric controller (500) are sealed in waterproof packages so that they are not visible in FIG. 5(b). The motion sensor (520) is drawn in dashed lines in FIG. 5(b) with dashed lined arrows pointing to the head direction and the face direction. FIG. 5(c) is a block diagram that shows the components of the electric controller (500). The intelligence of the electric controller (500) is provided by an integrated circuit (530). In this example, the integrated circuit (530) comprises a memory module (532) and a logic module (531). One example of the logic module is a programmable microcontroller. One example of the memory module is a FLASH nonvolatile memory device. The memory module (532) and the logic module (531) can be one integrated circuit chip in the same package, and can also be separated integrated circuit chips in separated packages. In this example, the integrated circuit is programmable through the Universal Serial Bus (USB) interface (529) shown in FIGS. 5(b, c). A computer or a mobile electronic device can be used to program the integrated circuit (530) using the USB interface (520). The power lines of the USB interface are connected to a rechargeable battery (539). The electric connection between the rechargeable battery (539) and the integrated circuit (530) is controlled by a power switch (525). This power switch (525) is a toggle switch on the front panel of the electric controller (500), as shown in FIG. 5(b). The mode-select switches (M1-M4) determine the operation mode of the integrated circuit (530); an exemplary list of operation modes is shown in FIG. 5(g). The volume control switches (521, 522) control the volume of the speaker (505). The channel-select switches (523, 524) can be used to select music to be played by the speaker (505). The switches mentioned above can also be contactless switches, such as magnetic switches. Contactless switches improve the water resistance of the device by minimizing the areas where water may enter the device and damage internal electrical components.

The logic module (531) of the integrated circuit (530) is able to analyze the outputs of the motion sensor (520) to determine the outputs of the integrated circuit (530), while the swimmer wearing the swimming goggle is swimming in water. The integrated circuit (530) is able to control the position of the reflector (513) and the light blocking cover (515) based on the motions of the swimmer detected by the motion sensor (520). The integrated circuit is also able to control the outputs of the electric sound speaker (505) while the swimmer wearing the swimming goggle is swimming in water.

Figure 5D:
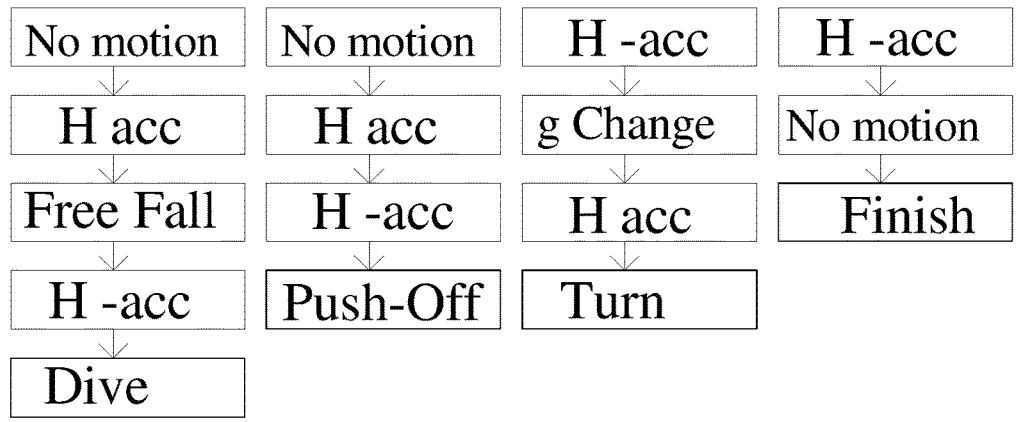
FIG. 5(d) is a symbolic block diagram illustrating how procedures are executed to determine the actions of a swimmer wearing a swimming goggle equipped with the electric controller in FIG. 5(c)
Figure 5D:
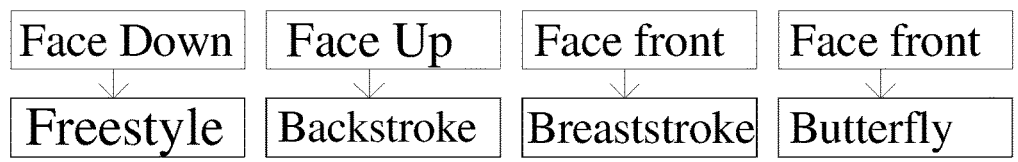

FIG. 5(d) is a simplified symbolic flow chart for the sequences of events used to determine the actions of the swimmer using the outputs of the motion sensor (520). In FIGS. 5(d-g), the symbol "H acc" means the motion sensor detected a large acceleration in the head direction, and the symbol "H −acc" means the motion sensor detected a large negative acceleration in the head direction. For example, if the motion sensor (520) detects no motion initially, followed by a large acceleration in head direction (H acc), followed by a free fall, and ending with a large negative acceleration in head direction (H −acc), then the logic module (531) of the integrated circuit (530) would know that the swimmer just dived into water. This process is shown in the first column of FIG. 5(d). If the motion sensor (520) detects no motion initially, followed by a large acceleration in head direction (H acc), and ending with a large negative acceleration in head direction (H −acc) without a free fall in between, then the logic module (531) of the integrated circuit (530) would know that the swimmer just pushed off the wall of a swimming pool. This process is shown in the second column of FIG. 5(d). If the motion sensor (520) detects a large negative acceleration in head direction (H −acc), followed by a change in direction of the gravity g force relative to the orientation of the motion sensor (520), and ending with a large acceleration in head direction (H acc), then the logic module (531) of the integrated circuit (530) would know that the swimmer just performed a flip turn. This process is shown in the third column of FIG. 5(d). If the motion sensor (520) detects a large negative acceleration in head direction (H −acc), which ended with no motion, then the logic module (531) of the integrated circuit (530) would know that the swimmer just finished swimming. This process is shown in the fourth column of FIG. 5(d). The motion sensor (520) also can tell the integrated circuit (530) the angle between gravity acceleration vector (g) relative to the face direction. When the swimming is swimming face down, the integrated circuit (530) would know that the swimmer is swimming freestyle; when the swimming is swimming face up, the integrated circuit (530) would know that the swimmer is swimming backstroke; and when the swimming is swimming with their face forwards for a period of time during each stroke, the integrated circuit (530) would know that the swimmer is swimming either breaststroke or butterfly, which can be distinguished by detailed analysis, as shown by the examples in FIG. 5(d).

Figure 5E:
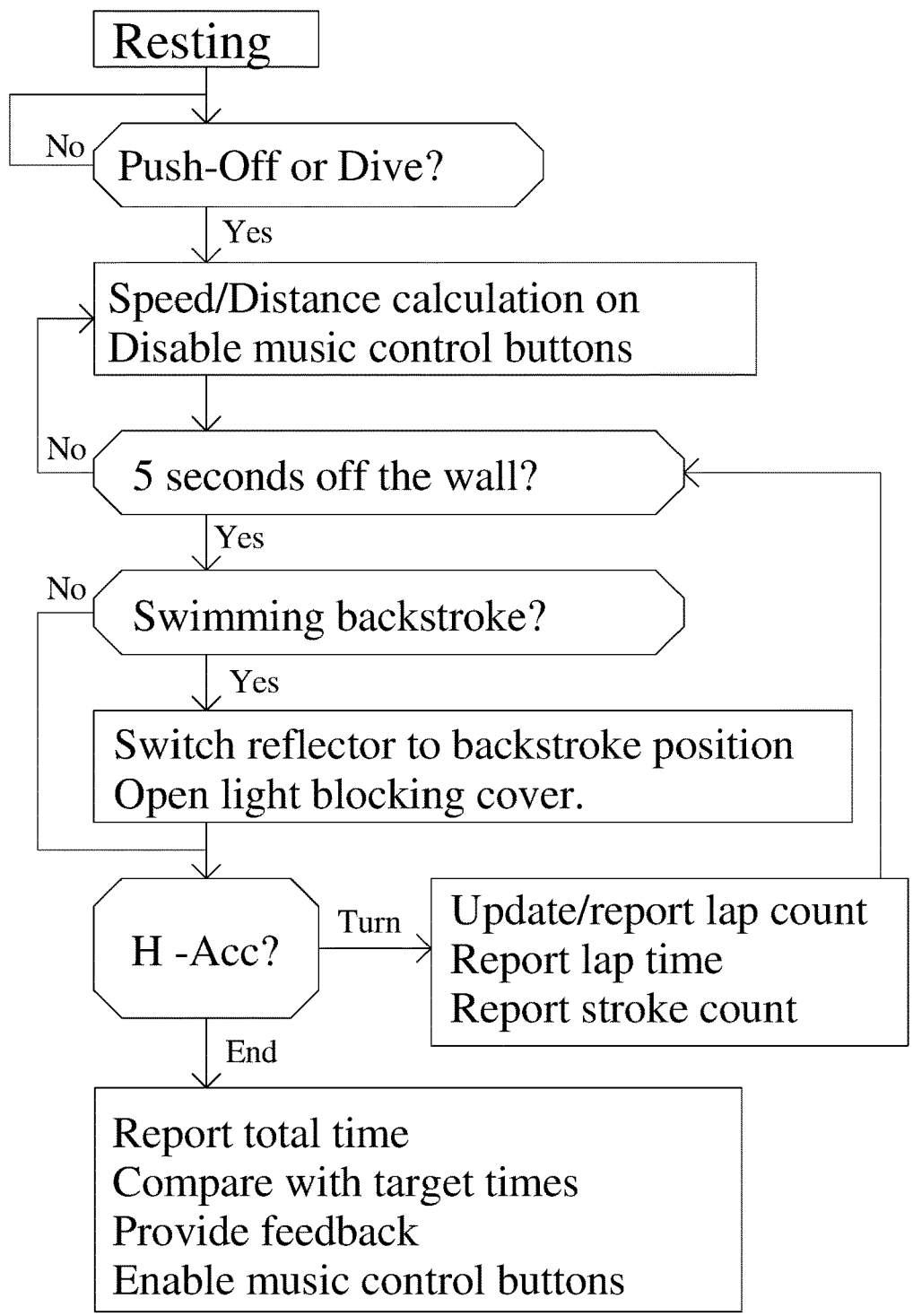
FIG. 5(e) is a flowchart for an exemplary application program used by the electric controller in FIG. 5(c)

Using the procedures in FIG. 5(d) to determine the actions of the swimmer, application programs stored in the non-volatile memory (532) of the integrated circuit (530) in the electric controller (500) can support sophisticated control of the light reflector (513), the light blocking cover (515), and the electric sound speaker (505). FIG. 5(e) is a flowchart for an exemplary application program used by the electric controller in FIG. 5(c). When a dive or push-off is detected after a resting state, the integrated circuit (530) starts to execute speed and distance calculations. If the motion sensor (520) is an accelerometer, speed can be calculated by integration of acceleration along head direction, and distance can be calculated by integration of speed. Using the electric sound speaker (505), the integrated circuit (530) also can play music that is stored in integrated circuit memory device (532). The volume and channel control buttons (521-524) also can be disabled to prevent accidental changes caused by water, which can exert forces against the buttons. Furthermore, the integrated circuit (530) would measure time using an internal timer, wait for 5 seconds, and check if the swimmer is swimming in backstroke or not by detecting face direction of the swimmer. If the swimmer is swimming backstroke, the integrated circuit (530) switches the light reflector (513) to backstroke position, and opens the light blocking cover (515) so that the swimmer can view the end of the swimming pool. The integrated circuit can also lap count. After the motion sensor (520) detects a large negative acceleration in the head direction (H −Acc), the integrated circuit (530) analyzes the next action of the swimmer. If the swimmer makes a turn, then the integrated circuit (530) updates the lap count, and reports the lap count to the swimmer using the electric sound speaker (505); optionally, the lap time and stroke count of the swimmer also can be reported to the swimmer at this time. If the swimmer stops swimming, then the integrated circuit (530) reports the total time to the swimmer using the electric sound speaker (505); optionally, the total time can be compared with target times, and the integrated circuit (530) can provide feedback such as encouraging words using the electric sound speaker (505); music also can be turned off, while the volume and channel control buttons (521-524) can be enabled at this time.

Figure 5F:
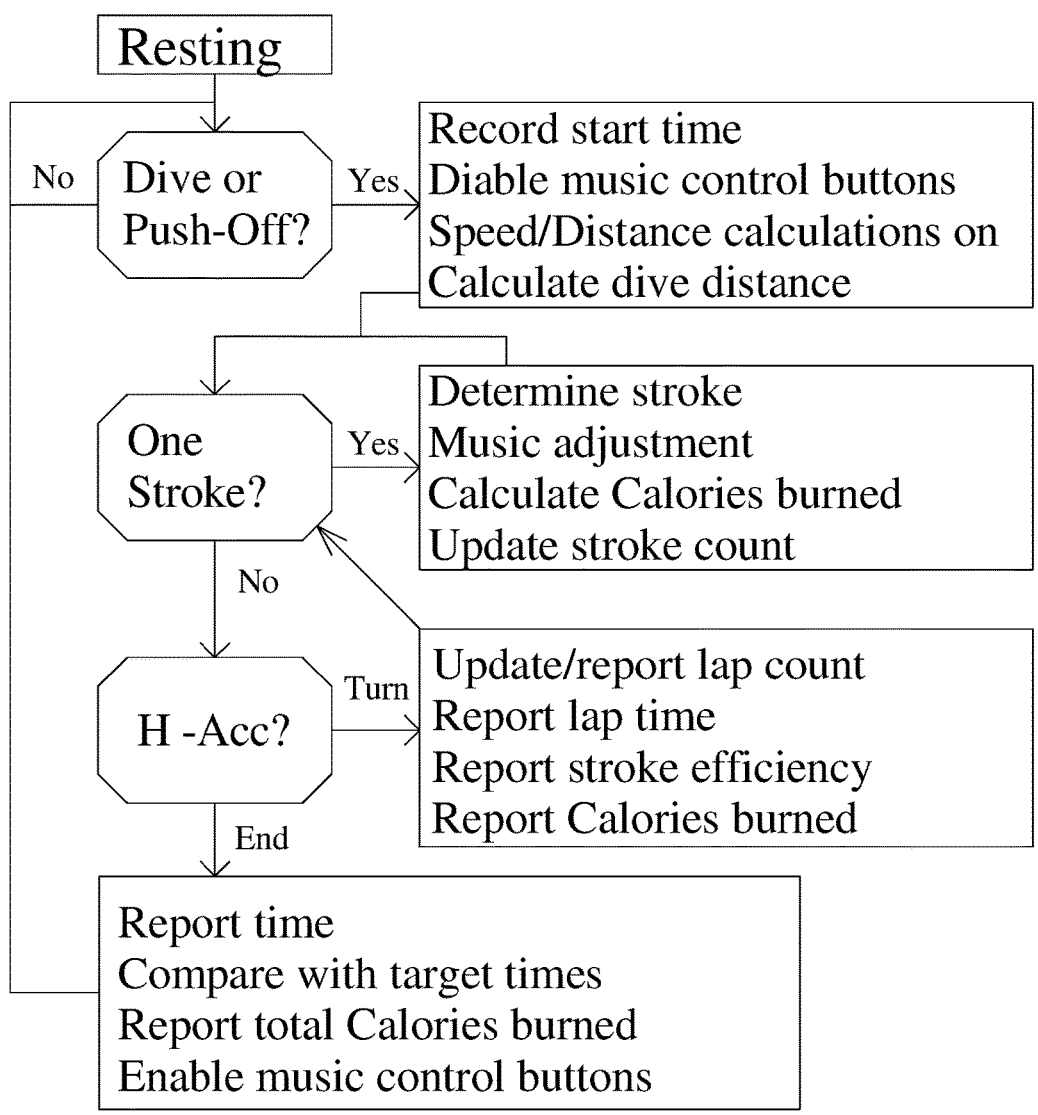
FIG. 5(f) is a flowchart for another exemplary application program used by the electric controller in FIG. 5(c)

FIG. 5(f) is a flowchart for another exemplary application program used by the electric controller in FIG. 5(c). In this example, when a push-off or a dive is detected after resting state, the integrated circuit (530) starts time measurement, disables volume and channel control buttons (521-524), and starts speed and distance calculations. It also can measure dive distance. After the swimmer takes a stroke, the integrated circuit (530) determines the stroke type and updates the stroke count. The integrated circuit (530) can also estimate the number of Calories burned by the swimmer based on the outputs of the motion sensor. Feedback can be provided using voice through the electric sound speaker (505). After the motion sensor (520) detects a large negative acceleration in the head direction (H −Acc), the integrated circuit (530) analyzes the next action of the swimmer. If the swimmer makes a turn, then the integrated circuit (530) will update the lap count, and report the lap count to the swimmer using the electric sound speaker (505); optionally, the lap time, stroke count, and Calories burned by the swimmer also can be reported at this time. If the swimmer stops swimming, then the integrated circuit (530) reports the total time to the swimmer using the electric sound speaker (505); optionally, the total time can be compared with target times, and the integrated circuit (530) can provide feedback such as encouraging words using the electric sound speaker (505). The total number of Calories burned by the swimmer can be reported, while the volume and channel control buttons (521-524) can be enabled at this time.

While the preferred embodiments have been illustrated and described herein, other modifications and changes will be evident to those skilled in the art. It is to be understood that there are many other possible modifications and implementations so that the scope of the invention is not limited by the specific embodiments discussed herein. Using a programmable integrated circuit, a swimming goggle equipped with an electric controller is capable of performing wide varieties of functions to support a swimmer wearing the swimming goggle. FIG. 5(g) shows a table that lists exemplary modes supported by the electric controller in FIG. 5(c). For example, when the mode-select switches (M1-M4) are set to be (0, 1, 0, 0), the electric sound speaker (505) is enabled to play music. The electric sound speaker (505) is able to change the way to play music depending on the motions of the swimmer wearing the swimming goggle. For example, when the mode-select switches (M1-M4) are set to be (0, 1, 1, 0), the electric sound speaker (505) plays music with a pace that is synchronized with the swimming pace of the swimmer; when the mode-select switches (M1-M4) are set to be (0, 1, 1, 1), the integrated circuit (630) adjusts the volume of the music played by the electric sound speaker (505) according to the swimming speed of the swimmer; when the mode-select switches (M1-M4) are set to be (1, 0, 1, 1), the integrated circuit (630) uses the electric sound speaker (505) to provide a voice report of the estimated number of Calories burned by the swimmer; and when the mode-select switches (M1-M4) are set to be (1, 1, 1, 1), the integrated circuit (630) store data to the non-volatile memory for further detailed analysis. The electric sound speaker of the swimming goggle is able to play music at a beat or a volume that is related to the motions of the swimmer wearing the swimming goggle. More examples are listed in FIG. 5(g).

The exemplary electronic controller (500) and the electric sound speaker (505) in FIG. 5(a) are embedded inside a swimming goggle. When the electronic controller is built-in as part of a swimming goggle, it is naturally inseparable from the goggle, which allows the controller to withstand forces exerted by the water while swimming. The disadvantage of having an embedded electric controller in a swimming goggle is that the controller will be useless once the goggle breaks or wears out. FIGS. 6(a-c) are simplified symbolic diagrams showing the structures of an exemplary electronic attachment for a swimming goggle that solves the problem. The electronic device (600) in this example is able to withstand strong forces in the water when swimmers are diving, turning, or swimming various strokes at high speeds. Furthermore, this electronic device (600) can be detached from the swimming goggle (650) so that the same electronic device can be used with different swimming goggles.

Figure 6A:
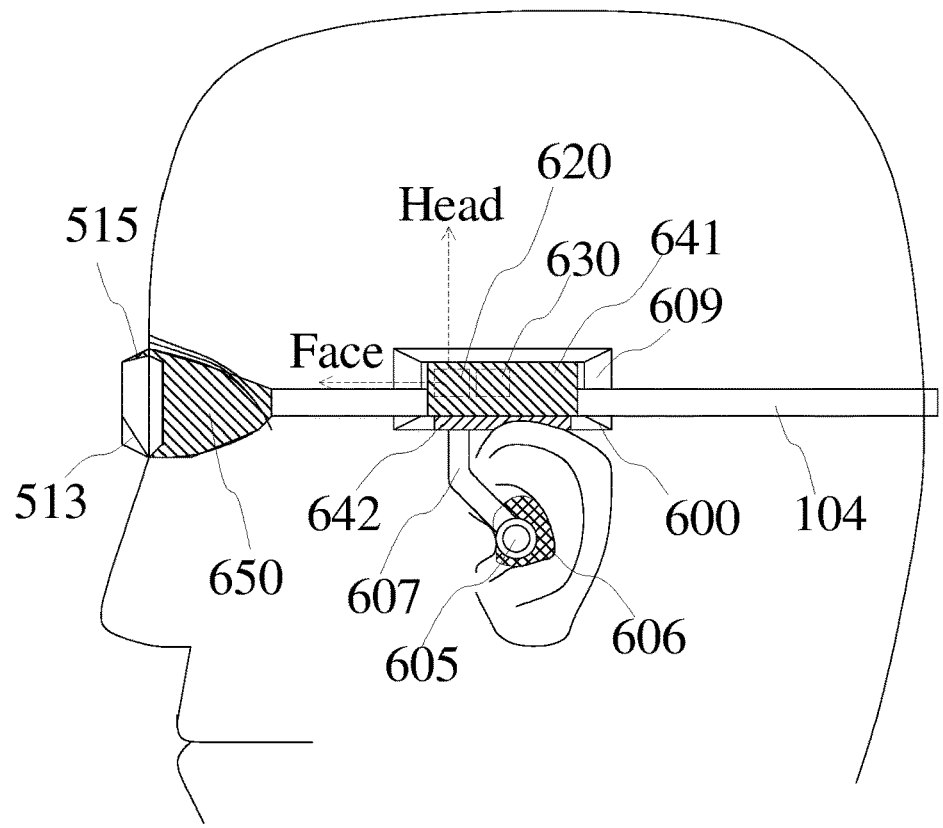
FIGS. 6(a-c) are simplified symbolic diagrams showing the structures of an exemplary electronic attachment for a swimming goggle.
FIG. 6(f) is a symbolic schematic diagram showing exemplary structures of the magnetic switch in FIGS. 6(d, e)
FIG. 6(g) is a simplified diagram illustrating exemplary input-output relationships of the magnetic switch in FIGS. 6(d, e)
Figures 6B, 6C:
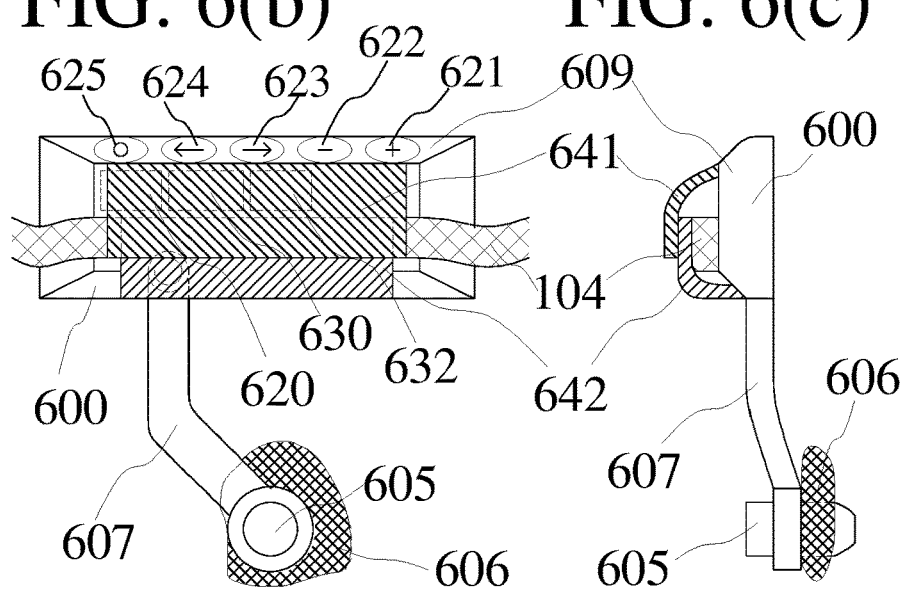
Figure 6D:
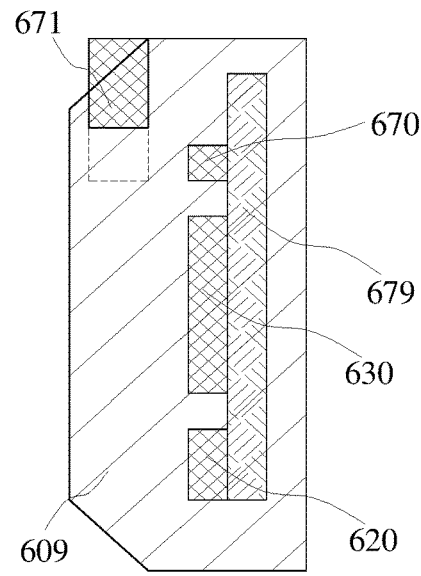
Figure 6E:
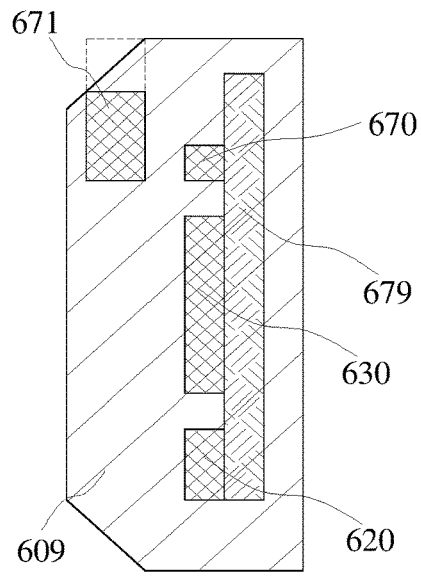
Figure 6F:
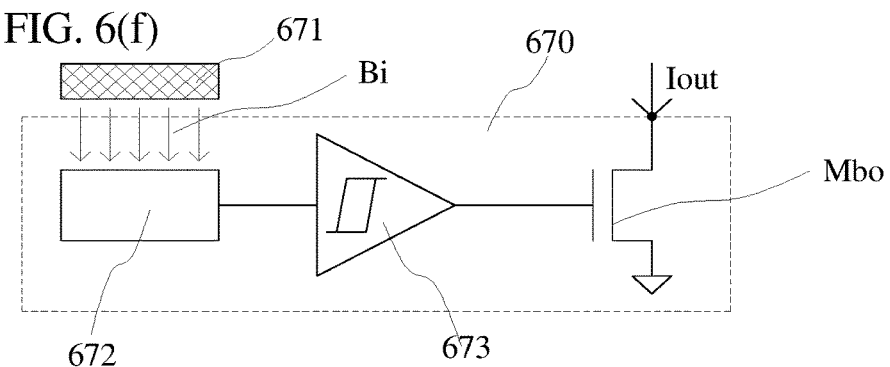
Figure 6G:
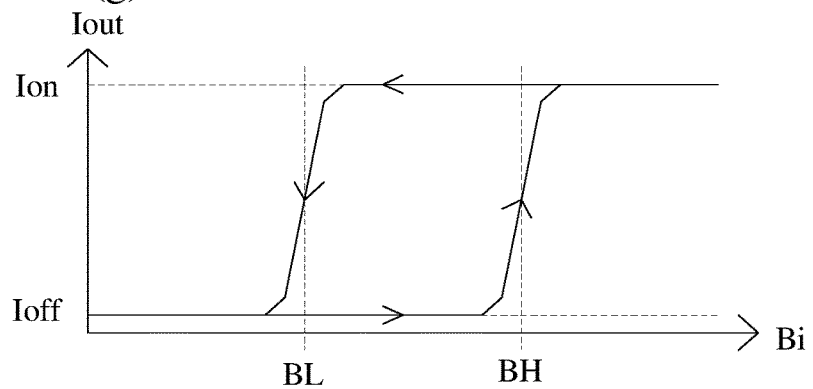

FIG. 6(a) is a simplified symbolic diagram showing a swimmer wearing a swimming goggle (650) with an electronic device (600) attached to the head strap (104) of the swimming goggle. For this example, the swimming goggle comprises an eye socket that has a transparent forward viewing window attached to a goggle frame, where the goggle frame has a backstroke viewing window opened on a top portion of the goggle frame disposed away from the transparent forward viewing window, and a position-switchable light blocking cover (515) attached to an edge of the backstroke viewing window. This light blocking cover (515) can switch position with respect to the edge of the backstroke viewing window. Its position is controlled electronically by the electronic device (600) that is attached to the swimming goggle. This swimming goggle (650) further comprises a position-switchable light reflector (513) that can switch positions with respect to the front viewing window of the eye socket. The position of the position-switchable light reflector (513) is controlled electronically by the electronic device (600) attached to the swimming goggle.

The electronic device (600) attached to the head strap (104) of the swimming goggle (650) comprises a motion sensor (620), an electric sound speaker (605), an integrated circuit (630), a waterproof package (609) that encloses the motion sensor (650) and the integrated circuit (630), and a connector to attach the waterproof package (609) to the head strap (104) of a swimming goggle (650). In this example, a loop Velcro (641) and a hook Velcro (642) wrap around the head strap (104) of the swimming goggle (650) to provide a reliable attachment between the waterproof package (609) and the head strap (104) of the swimming goggle (650), as shown in FIGS. 6(*a-c*). The waterproof package (609) also can enclose other components such as a USB interface socket, none-volatile memory device (632), battery, power switches, and other control switches. As shown in FIG. 6(*b*), the front panel of the waterproof package (609) comprises two volume control switches (621-622), two channel-select switches (623, 624), and a power switch (625); it can also have a USB interface socket and mode-select switches placed at the back side of the package. A motion sensor (620) is placed inside the electronic device (600) as shown by the dashed lines in FIG. 6(*a*). While in use, this motion sensor (620) is attached near the ear of the swimmer, where its x axis is pointing towards the "face direction", and its y axis is pointing towards the "head direction", as illustrated by the dashed lined arrows in FIG. 6(*a*). The integrated circuit (630) in the electronic device (600) is able to read the outputs of the motion sensor (620) and analyze the motions of the swimmer wearing the swimming goggles with the attached electronic device while the swimmer is swimming in water. The electronic device (600) illustrated in FIGS. 6(*a-c*) comprises all the components of the electronic controller (500) described in FIGS. 5(*a-c*). Therefore, it is able to support all the functions described in FIGS. 5(*d-g*).

For the example in FIGS. 6(*a-c*), the electrical sound speaker (605) is placed inside an earbud. Typical earbuds would easily fall out while the swimmer is swimming in water. The electrical sound speaker (605) in this example is placed inside an earbud that has a moldable ear tip (606), as shown in FIGS. 6(*a-c*). This moldable ear tip (606) can be molded into different shapes in order to tightly fit the external ear canal of different users. In addition, the earbud (605) is connected to the waterproof package (609) of the electronic device with a solid elastic connector (607). This elastic connector (607) provides an elastic force that helps push the earbud into the external ear canal of the swimmer, as illustrated in FIGS. 6(*a-c*). As a result, the earbud (605) will not fall out when the swimmer is diving, turning, or swimming at high speed.

The applicant has built prototypes of the present invention. When selection switches (621-625) are implemented by mechanical switches, the waterproof package (609) will need to have movable structures at the positions of those switches (621-625). Such moveable structures could include buttons, but experimental results show that the positions of the selection switches often become weak points that degrade waterproof properties, since water is more likely to seep into the device through the moveable structures. It is therefore highly desirable to use contactless switches as selection switches in order to prevent this problem. FIGS. 6(*d, e*) are cross section diagrams showing exemplary structures when the wearable electronic device in FIG. 6(*a-c*) is using magnetic switches. In this example, a magnetic switch (670), an integrated circuit (630), and a motion sensor (620) are mounted on a printed circuit board (679). These electrical components (620, 630, 670) are completely enclosed by a waterproof package (609), as shown in FIGS. 6(*d, e*). A magnet (671) is placed close to the magnetic switch (670) without making direct contact. When the magnet (671) is in its initial position at a distance away from the magnetic switch (670), the magnetic field detected by the magnetic switch (670) will remain weak, causing the magnetic switch to remain off, as illustrated by the situation in FIG. 6(*d*). When the magnet (671) is pushed to a position near the magnetic switch (670), the magnetic field detected by the magnetic switch (670) will become strong, causing the magnetic switch to turn on, as illustrated by the situation in FIG. 6(*e*). By changing the position of the magnet (671), the user of the wearable electronic device in FIGS. 6(*a-c*) can control the operations of the wearable electronic device. For example, the user can pause or play the music played by the electrical sound speaker (605), increase or decrease the volume of the music, skip one music file forward, skip one music file backward, connect to Bluetooth devices, or execute other operations by changing the position of the magnet (671) relative to the position of the magnetic switch (670). Furthermore, if the wearable electronic device has multiple preprogrammed functionalities built into it, the user can also change the position of the magnet to switch between these functionalities. To support more complex operations, the wearable electronic device can have multiple magnetic switches or multiple magnets. Because the magnet (671) does not need to make physical contact with the magnetic switch (670), the waterproof package (609) does not need to have moving parts, effectively removing critical points of weak water resistance. Using magnetic switches, the waterproof package (609) can consistently meet the IPX7 water resistance standard, meaning that the waterproof package can stay under one meter of water for 30 minutes without enduring any damages to the electrical components enclosed by the waterproof package. The waterproof package (609) can further pass more thorough tests such as sustaining a three-meter free fall into water, followed by continuous submersion under three-meter deep water for 30 minutes, without enduring damages to the electrical components enclosed by the waterproof package.

FIG. 6(*f*) is a symbolic schematic diagram showing exemplary structures of the magnetic switch (670) in FIGS. 6(*d, e*). In this example, the magnetic switch (670) comprises a Hall effect magnetic sensor (672), a comparator with Schmitt trigger property (673), and an output switch (Mbo). The Hall effect sensor (672) detects magnetic field (Bi) from a nearby magnet (671), and outputs an electrical signal that typically has a linear relationship with the amplitude of the detected magnetic field (Bi). A comparator (673) compares the output of the Hall effect magnetic sensor (672) with reference voltages, and either turns on or turns off the output switch (Mbo), as illustrated in FIG. 6(*f*). When this switch (670) is off, the output current (Iout) decreases to an asymptotic small leakage current (Ioff), which is typically less than a few microamps. When the switch (670) is turned on, it is able to produce significant output current (Ion), which is typically greater than one milliamp.

To avoid output bouncing while switching events, it is highly desirable for the magnetic switch (670) to have a hysteresis input-output relationship as illustrated in FIG. 6(*g*). The magnetic switch is turned on (Iout=Ion) when the magnitude of the magnetic field (Bi) detected by the magnetic switch is higher than a manufacturer defined upper threshold value (BH); the magnetic switch is turned off (Iout=Ioff) when the magnitude of the magnetic field (Bi) detected by the magnetic switch is less than a manufacturer defined lower threshold value (BL), where BL is less than BH. When the magnetic switch is already on, it remains on until Bi becomes less than BL; when the magnetic switch is already off, it remains off until Bi becomes greater than BH, as illustrate in FIG. 6(g).

Figure 7A:
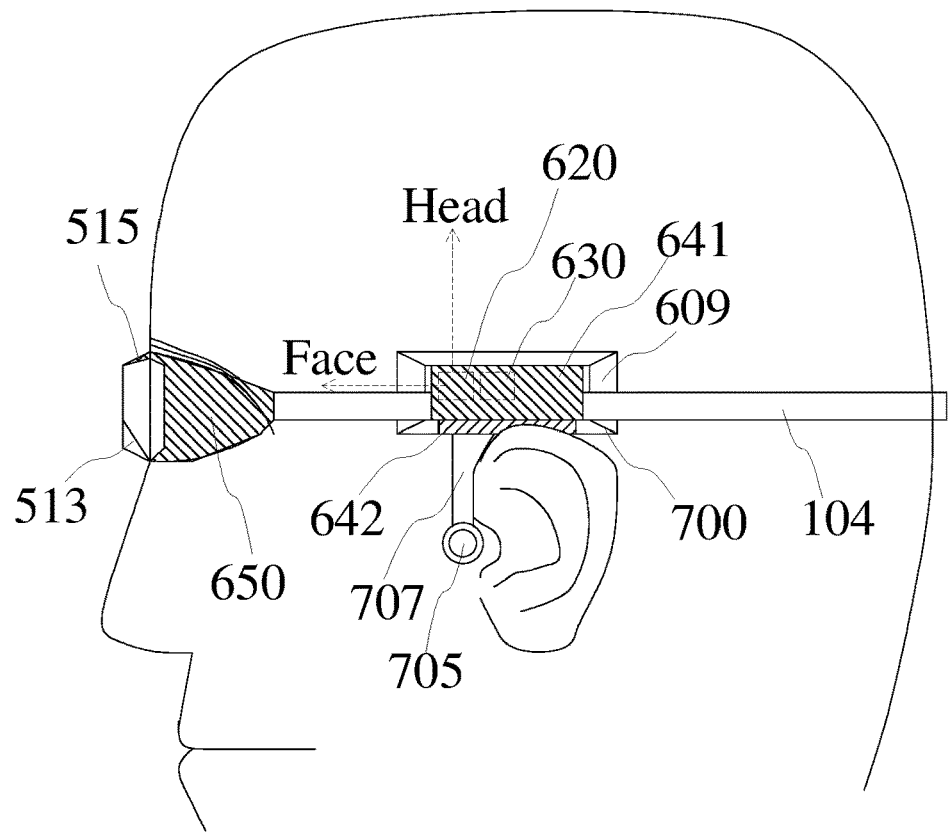
FIGS. 7(a-c) are simplified symbolic diagrams showing the structures of another exemplary electronic attachment for a swimming goggle.
Figures 7B, 7C:
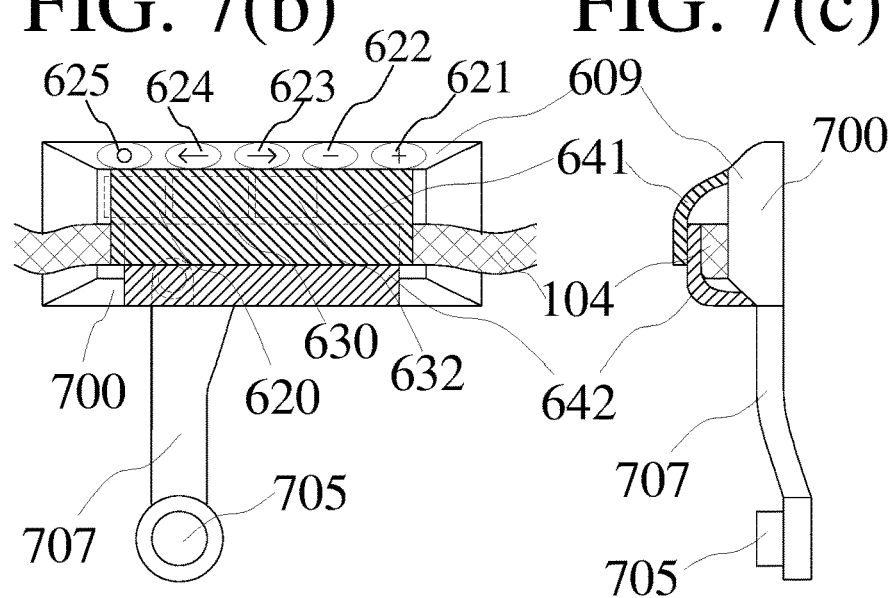

FIGS. 7(a-c) are simplified symbolic diagrams showing the structures of another exemplary electronic attachment for a swimming goggle. The structures of the electronic device (700) in FIGS. 7(a-c) are almost identical to those of the electronic device (600) in FIGS. 6(a-c), except for the supporting structures of the electrical sound speaker (705). For this example, the electrical sound speaker (705) of the electronic device (700) is attached to the waterproof package (609) of the electronic device (700) with a sold elastic connector (707), and the electrical sound speaker (705) is pressed onto the side of the head of the swimmer, as shown in FIGS. 7(a-c). In this way, the electrical sound speaker (705) can function reliably when the swimmer is diving, turning, or swimming at high speed.

Figure 8A:
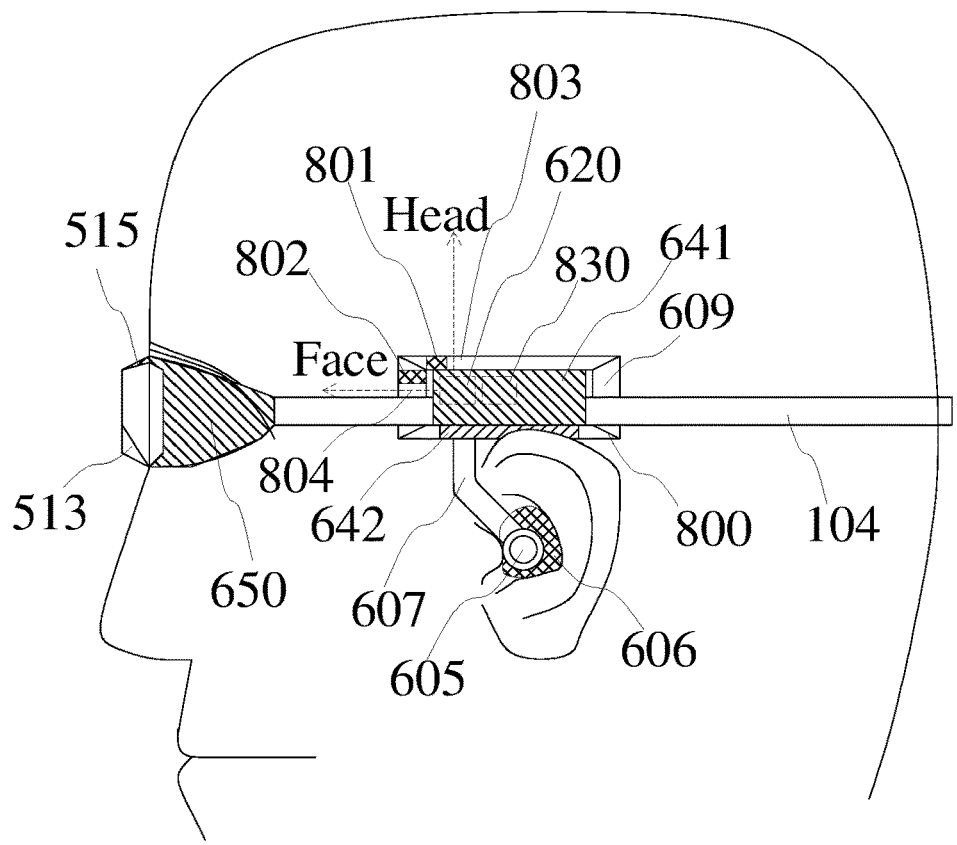
FIGS. 8(a-g) are exemplary symbolic diagrams illustrating the structures of electronic devices equipped with flow meters that are attached to athletic headgear.
FIG. 8(h) is a simplified diagram showing the structures of an exemplary wearable electronic device attached to a swimming goggle.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, accelerometers are one type of motion sensors that can support applications of the present invention, but other types of devices also can be used to analyze the activities of users. FIGS. 8(a, b) are simplified symbolic diagrams showing the structures of another exemplary electronic device attached to a swimming goggle. The structures of the electronic device (800) in FIGS. 8(a, b) are almost identical to those of the electronic device (600) in FIGS. 6(a-c). The difference is that the device has two flow meters (801, 802) placed near the upper left corner of the electronic device (800). As illustrated in FIG. 8(a), one flow meter (801) is placed on the upper side wall (803) of the electronic device (800), so that it can measure the component of the fluid speed along the "head" direction, while the other flow meter (802) is placed on the left side wall (804) of the electronic device (800), so that it can measure the component of the fluid speed along the "face" direction. These two flow meters (801, 802) can therefore measure the fluid speed as a two-dimensional vector.

Figure 8B:
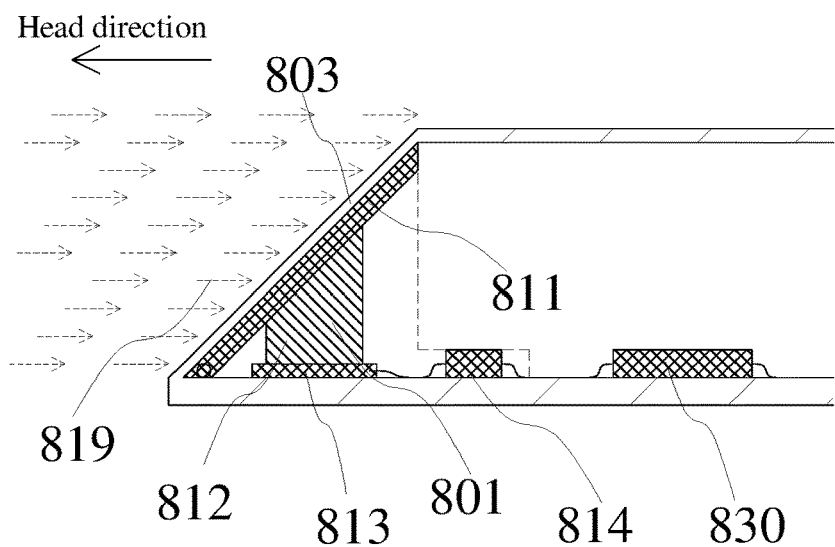

FIG. 8(b) is a simplified symbolic diagram illustrating the structures for one (801) of the flow meters (801, 802) in FIG. 8(a). The direction of the fluid flow (819, 835, 845) is represented symbolically by dashed-lined arrows in FIGs. (b, d, f). Examples of fluid flows are water flows caused by the motions of swimmers or air flows caused by the motions of cyclists or runners. For the example in FIG. 8(b), when fluid flow (819) along the "face" direction impacts the upper side-wall (803) of the electronic device (800), the fluid flow (810) produces a force on the upper side-wall (803). In this example, the upper side wall (803) is made of flexible plastic material so that the force produced by the relative fluid flow (819) pushes against a solid plate (811) placed underneath the side wall (803), as shown in FIG. 8(b). The resulting force on the upper side-wall (803) passes through the solid plate (811) and a pillar (812) to be measured by a pressure sensor (813), as illustrated in FIG. 8(b). One example of a pressure sensor that can be used for this application is a piezoelectric device. The output of the pressure sensor (813) is amplified by a linear amplifier (814), and the output of the linear amplifier (814) is connected to an input of an integrated circuit (830). This integrated circuit (830) analyzes the electric outputs of the linear amplifier (814) to determine the speed of the fluid flow (819), which provides an accurate measurement on the speed of body motions. This fluid speed measurement provides one of the factors used to analyze the actions of the user wearing the electronic device (800). For this example, the structures (803, 811, 812) that transfers fluid pressure, the pressure sensor (813), and the linear amplifier (814) form a flow meter. The other flow meter (802) shown in FIG. 8(a) can have similar or different structures.

Figure 9A:
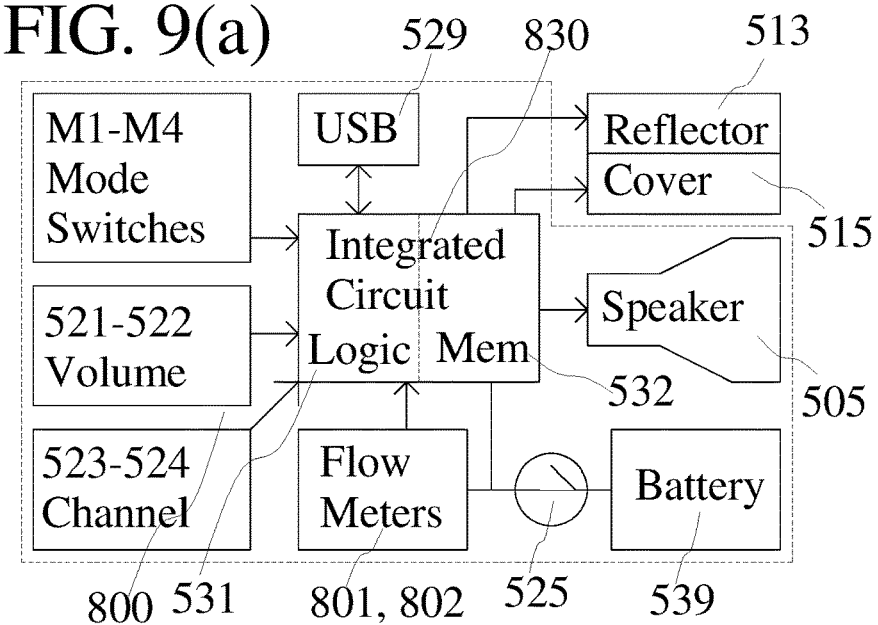
FIGS. 9(a-c) are exemplary symbolic block diagrams for the electronic devices of the present invention.
FIG. 9(c) is a symbolic block diagram showing the structures of the wearable electronic device in FIG. 8(h).

FIG. 9(a) is a simplified block diagram that shows the components of the electronic device (800) in FIG. 8(a). The structures of this electronic device (800) are nearly the same as those of the electronic controller (500) shown in FIG. 5(c), except that this electronic device (800) comprises flow meters (801, 802), and that the intelligence of the electronic device (800) is provided by an integrated circuit (830) that is able to analyze the outputs of the flow meters (801, 802). In this example, the integrated circuit (830) also comprises a memory module (532) and a logic module (531). One example of a logic module is a programmable microcontroller. One example of a memory module is a FLASH nonvolatile memory device. The memory module (532) and the logic module (531) can be one integrated circuit chip in the same package, and can also be separated integrated circuit chips in separated packages. In this example, the integrated circuit is programmable through the Universal Serial Bus (USB) interface (529). A computer or a mobile electronic device can be used to program the integrated circuit (830) using the USB interface (529). The logic module (531) of the integrated circuit (830) is able to analyze the outputs of the flow meters (801, 802) to determine the outputs of the integrated circuit (830) while the user wearing the electronic device (800) is in action. The integrated circuit (830) is able to control the position of the reflector (513) and the light blocking cover (515) of the swimming goggle based on the motions of the user detected by the flow meters (801, 802). The integrated circuit is also able to control the outputs of the electrical sound speaker (505) while the user wearing the electronic device (800) is swimming, biking, running, or doing other physical activities.

FIG. 5(h) is a simplified symbolic flow chart for the sequences of events used to determine the actions of the swimmer wearing the electronic device (800) in FIGS. 9(a, b). In FIG. 5(h), the symbol "H+v" means that the flow meters detected a brief and sudden interval of high speed fluid flow in the head direction; the symbol "H−v" means that the flow meters detected a decrease in velocity in the head direction; the symbol "Hv" means that the flow meters detected regular speed in the head direction; the symbol "Fv" means that the flow meters detected fluid flow in the face direction; the symbol "HFv" means that the flow meters detected fluid flow in both the head direction and face direction; and the symbol "complex v" means that the flow meters detected complex fluid flows in both the head direction and face direction due to complex actions such as diving into water, or performing a turn. For example, if the flow meters (801, 802) detect no initial motion, followed by complex fluid flows (complex v), followed by a brief and sudden interval of high speed fluid flow in the head direction (H+v), and ending with regular speed in the head direction (Hv), then the integrated circuit (830) would know that the swimmer just dived into water. This process is shown in the first column of FIG. 5(h). If the flow meters (801, 802) detect no initial motion, followed by a brief and sudden interval of high speed fluid flow in the head direction (H+v) without severely complex fluid flows, and ending with regular speed in the head direction (Hv), then the integrated circuit (830) would know that the swimmer just pushed off the wall of a swimming pool. This process is shown in the second column of FIG. 5(h). If the flow meters (801, 802) detect a decrease in velocity in the head direction (H−v), followed by complex fluid flows (complex v), and ending with a brief and sudden interval of high speed fluid flow in the head direction (H+v), then the integrated circuit (830) would know that the swimmer just performed a turn. This process is shown in the third column of FIG. 5(h). If the flow meters (801, 802) detect a decrease in velocity in the head direction (H−v), which eventually ends with no motion, then the integrated circuit (830) would know that the swimmer just finished swimming. This process is shown in the fourth column of FIG. 5(h). When the swimmer is swimming with regular speed in the head direction and breathes sideways (Hv Side breath), then the integrated circuit (830) would know that the swimmer is swimming freestyle; when the swimmer is swimming with regular speed in the head direction and breathes facing skywards (Hv Up breath), then the integrated circuit (830) would know that the swimmer is swimming backstroke; when the flow meters (801, 802) detect an interval of head direction flow and an interval of face direction flow (Hv−Fv) during each armstroke, then the integrated circuit (830) would know that the swimmer is swimming either breaststroke or butterfly, which can be distinguished by detailed analysis.

Using the procedures in FIG. 5(h) to determine the actions of the swimmer, application programs stored in the nonvolatile memory (532) of the integrated circuit (830) in the electronic device (800) can support sophisticated control of the light reflector (513), the light blocking cover (515), and the electric sound speaker (505). The integrated circuit (830) would be able to support all the analyses shown in FIGS. 5(e-g). Furthermore, the integrated circuit would also be able to analyze the actions of cyclists, runners, and users of other athletic gear using the procedures in FIG. 5(h). Changes in fluid speed measured by the flow meters will similarly correspond to specific actions performed by cyclists and runners. Accelerometers can also be used in place of flow meters to analyze such actions-certain patterns in accelerations can similarly be used to detect specific actions performed by swimmers, runners, cyclists, and users of other athletic gear. Furthermore, sound generating or wave emitting devices can be attached to athletic gear to emit signals that are picked up by a microphone integrated into the electronic device. This would also allow for the analysis of specific actions performed by runners, cyclists, and users of other athletic gear on land.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, the flow meter (801) in the above examples measures fluid pressure on the side wall (803), but other types of flow meters can be used to analyze the activities of the users as well. The electronic device (800) in FIGS. 8(a, b) is attached to a swimming goggle, while electronic devices with flow meters also can attach to other types of athletic headgear. FIGS. 8(c, d) are simplified symbolic diagrams showing the structures of another exemplary electronic device (820) attached to a sweat band (821). The structures of the electronic device (820) in FIGS. 8(c, d) are almost identical to those of the electronic device (800) in FIGS. 8(a, b). These are the differences: it is attached to a sweat band (821) with velcro (822), and it has a flow meter (825) that measures fluid speed using Bernoulli's Principle.

Figure 8C:
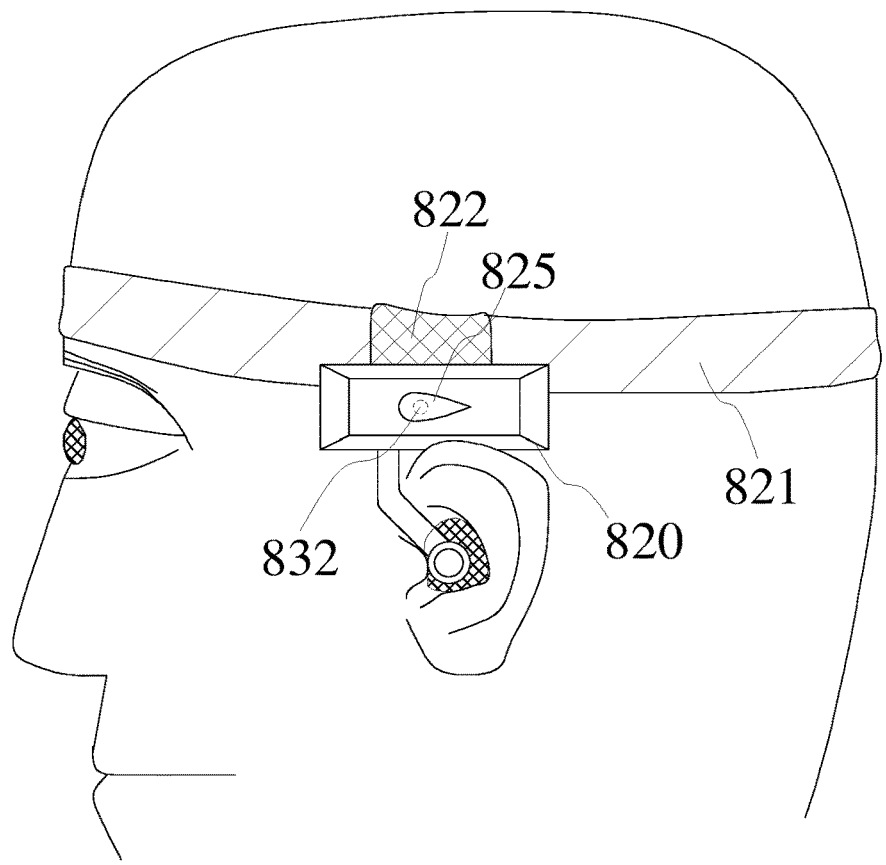
Figure 8D:
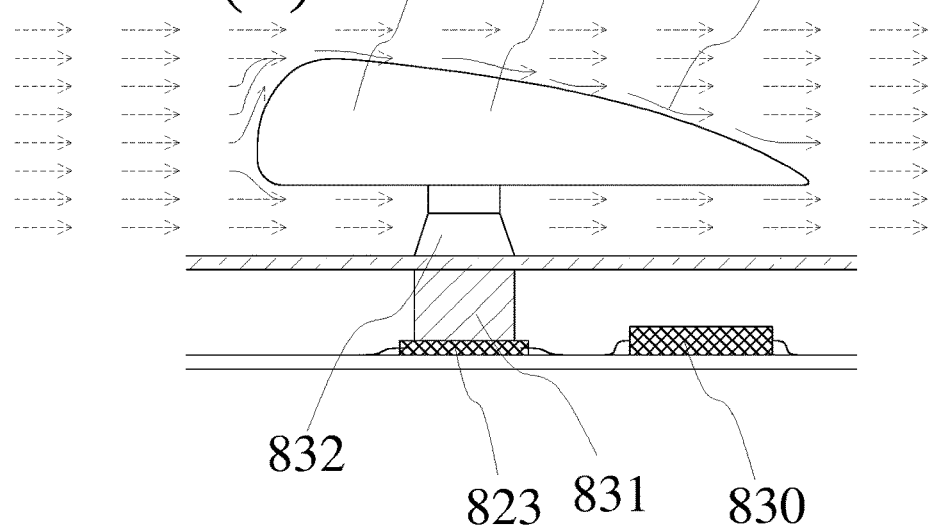

FIG. 8(d) is a simplified symbolic cross-section diagram illustrating the structures of the flow meter (825) in FIG. 8(c). This flow meter (825) comprises a sensing wing (834) with cross-section structures similar to those of an airplane wing. When fluid (835) passes through this sensor wing (834), a lifting force is produced on the wing due to Bernoulli's Principle. This lifting force is transferred through a pole (832) outside of the package of the electronic device (820) and a pillar (831) inside of the electronic device (820) to a pressure sensor (823), as illustrated in FIG. 8(d). The output of the pressure sensor (823) is connected to an input of an integrated circuit (830). This integrated circuit (830) analyzes the electric outputs of the pressure sensor (823) to determine the speed of the fluid flow (835) as one of the factors used to analyze the actions of the user wearing the electronic device (820). For this example, the sensor wing (834), the structures (832, 831) that transfer lifting forces, and the pressure sensor (823) form a flow meter. The components of this electronic device (820) can be similar to that in FIG. 9(a), except that the device uses a different type of flow meter (825).

FIGS. 8(e-g) are simplified symbolic diagrams showing the structures of another exemplary electronic device (840) attached to a bicycle helmet (841). The structures of the electronic device (840) in FIGS. 8(e, f) are almost identical to those of the electronic device (820) in FIGS. 8(c, d). These are the differences: the device is attached to a bicycle helmet (841) with velcro (842), it has a flow meter (845) that measures fluid speed using a rotational turbine (846), and it is equipped with an inclinometer (852). An inclinometer is an instrument for measuring angles of slope (or tilt), elevation or depression of an object with respect to gravity.

FIG. 8(f) is a simplified symbolic cross-section diagram illustrating the structures of the flow meter (845) and the inclinometer meter (852) in FIG. 8(e). This flow meter (845) comprises a rotational turbine (846). When fluid (859) passes through this rotational turbine (846), the rotational speed of the turbine (846) provides a measure of the fluid speed; rotational rate of the turbine (846) measures speed while number of rotations of the turbine (846) measures distance. In addition, the turbine (846) also provides energy to an electric power generator (847) that is able to generate electric power to re-charge the battery (530) in the electronic device (840). Other types of rotational structures, such as paddle wheels, also can serve similar functions. The turbine (846) in this example is mounted on a rotational axis (850) so that the flow meter (845) is always pointing in the direction of fluid flow. FIG. 8(f) shows a situation when the fluid flow (846) is in a different direction.

For a bicyclist, the energy needed to ride a bike is not only dependent on speed, but is also dependent on the slope of the road. It is therefore desirable to be able to measure the slope of the road. Therefore, the electronic device in FIGS. 8(e-g) is equipped with an inclinometer (852). For this example, the inclinometer (852) comprises a weight (851) attached to a rod (853) that can rotate freely against a rotational axis (850). Due to the force of gravity on the weight (851), this inclinometer (852) is always pointing downward. When the bicyclist is riding on a flat road, the inclinometer and the flow meter (845) are perpendicular to each other, as illustrated in FIG. 8(f). When the bicyclist is riding uphill, the angle between the flow meter (845) and the inclinometer (852) is obtuse, as illustrated in FIG. 8(g). When the bicyclist is riding downhill, the angle between the flow meter (845) and the inclinometer (852) is acute. Therefore, the slope of road can be measured by measuring the angle between the flow meter (845) and the inclinometer (852).

Figure 8H:
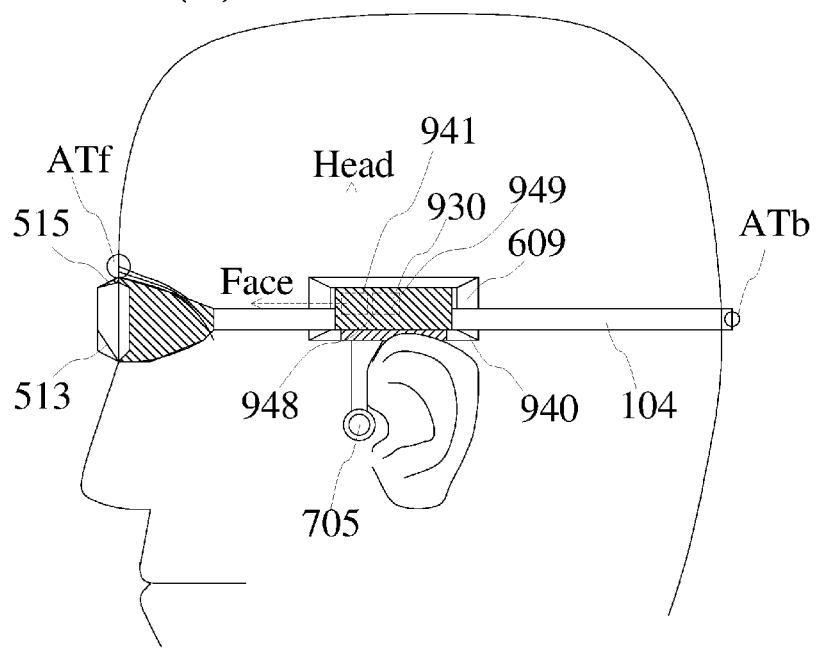
Figure 9B:
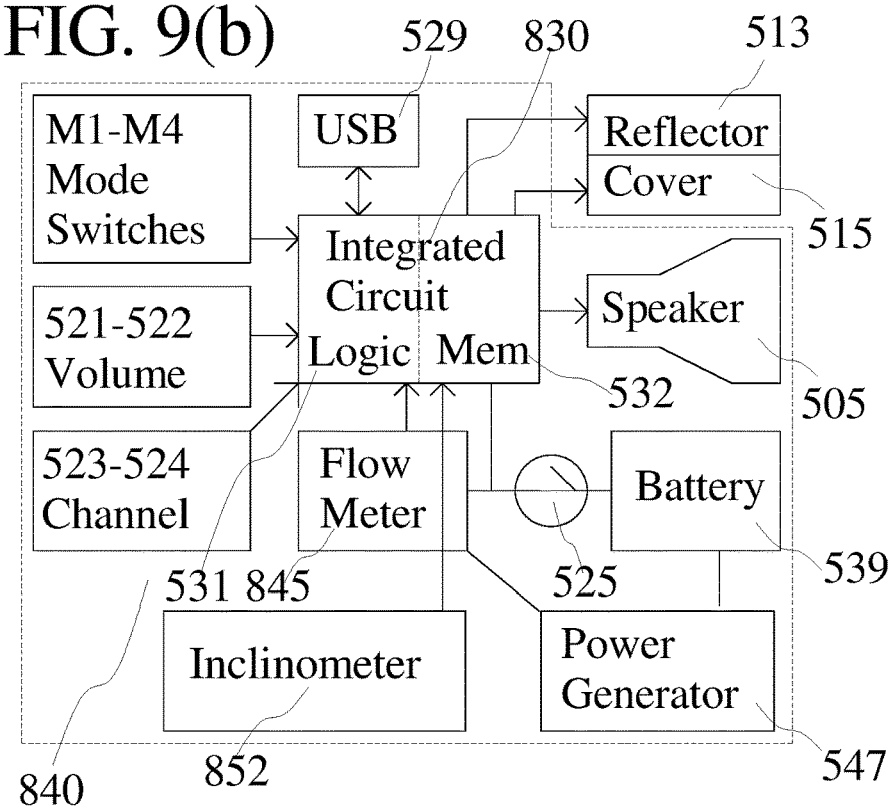

FIG. 9(b) is a simplified symbolic block diagram showing the structures of the electronic device (840) in FIGS. 8(e-g). The structures of this electronic device (840) are nearly the same as those of the electronic device (800) shown in FIG. 9(a). The differences are that this electronic device (840) comprises a different type of flow meter (845), and that it has an inclinometer (852) and a power generator (547). The electric power generator (547) utilizes the energy provided by the flow meter (845) to charge the battery (539), as shown in FIG. 9(b). In this example, the integrated circuit (830) also comprises a memory module (532) and a logic module (531). The logic module (531) of the integrated circuit (830) is able to analyze the outputs of the flow meter (845) to determine the outputs of the integrated circuit (830) while the user wearing the electronic device (840) is in action. The integrated circuit (830) can determine the slope of the road by measuring the angles between the flow meter (845) and the inclinometer (852) when the electronic device (840) is used by a bicyclist or a runner. The integrated circuit is also able to control the outputs of the electric sound speaker (505) while the user wearing the electronic device (840) is swimming, biking, running, or doing some other exercise.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, the electrical devices in above examples used USB wired interface to communicate with external electrical devices, while wireless communication also can be used for external communication.

Figure 3C:
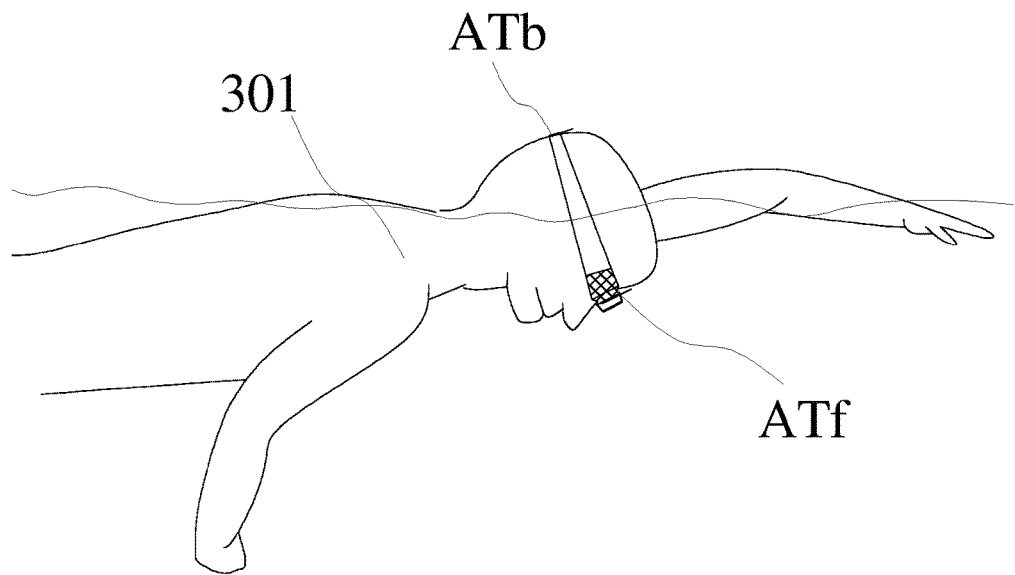
FIG. 3(c) shows a simplified view of a user who is swimming freestyle with his face facing towards the bottom of the pool while wearing an electronic device with two antennas.
Figure 3D:
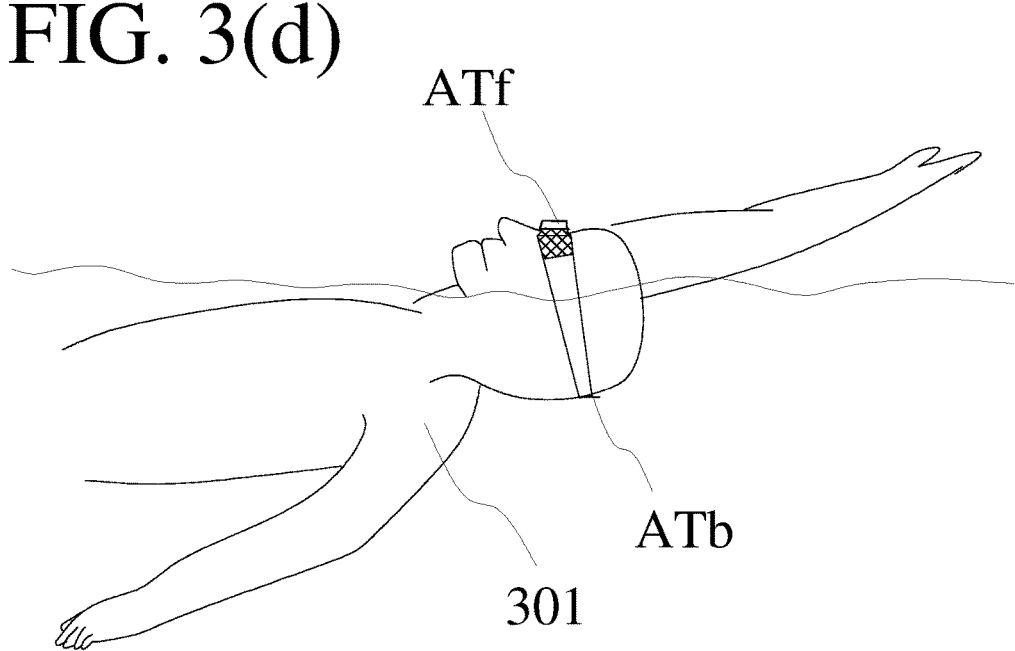
FIG. 3(d) shows a simplified view of a user who is swimming backstroke on his back facing towards the sky while wearing an electronic device with two antennas.
Figure 9C:
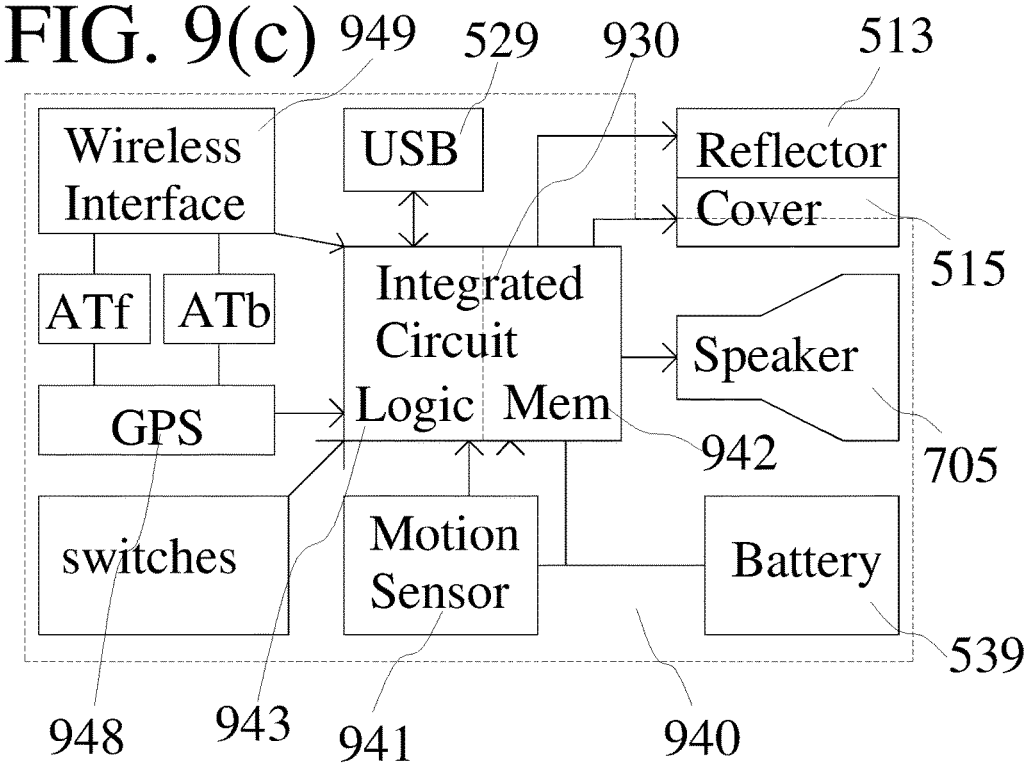

FIG. 8(h) is a simplified symbolic diagram showing the structures of an exemplary wearable electronic device (940) attached to a swimming goggle, and FIG. 9(c) is a symbolic block diagram for the structures of the wearable electronic device (940) in FIG. 8(h). The structures of this wearable electronic device (940) are similar to those of the electronic device (800) in FIG. 8(a) and FIG. 9(a). The major difference is that this device (940) has a wireless interface device (949) for communicating with external electronic devices, as well as an electronic device (948) that receives Global Positioning System (GPS) signals. These wireless electronic devices (948, 949) can be part of the integrated circuit (930) that works with the electrical sound speaker (705), motion sensor (941), switches, reflector (513), and cover (515), but can alternatively be separate devices. These wireless devices (948, 949) are connected to two antennas (ATb, ATf). Because wireless signal transfers do not typically function properly when the antenna is submerged in water, it is desirable to have two or more antennas to ensure that there is at least one antenna above the water for the majority of the time. As a result, one antenna (ATb) is placed near the back of the head of the swimmer so that this antenna (ATb) is above water the majority of the time when the swimmer wearing the wearable electronic device is facing down towards the bottom of the pool or body of water, and is not completely submerged underwater, as illustrated in FIG. 3(c). Another antenna (ATf) is placed near the forehead of the swimmer so that this antenna (ATf) is above water the majority of the time when the swimmer wearing the wearable electronic device is facing up towards the sky, and is not completely submerged underwater, as illustrated in FIG. 3(d). Although one of the antennas (ATf, ATb) may be submerged, the wearable electronic device (940) can determine which antenna currently possesses the more reliable signal based on the swimming actions or head orientation of the user wearing the wearable electronic device. The wearable electronic device (940) can also have a wired USB interface (529) for communicating with other external electronic devices.

In the wearable electronic device (940) in FIG. 8(h), one of the measurement axes of the motion sensor points in a direction that is close to that of the front viewing direction (Face direction) of the swimming goggle worn by the user wearing the wearable electronic device. As a result, the motion sensor (941) can detect the head orientation of the swimmer relative to the direction of the gravity acceleration vector (g). By using the outputs of the motion sensor (941), the logic circuits (943) in the integrated circuit (930) can determine the swimming stroke that the user wearing the wearable electronic device (940) is swimming, as illustrated by previous examples. Swimming data, such as the swimming times of the user, can be stored in an electrical memory device (942). Swimming times are defined as the time it takes for an individual to swim a certain distance using a specific swimming stroke or a specific format of swimming strokes such as that of the individual medley. Swimming data can include, but are not limited to, Calories burned while swimming, swimming times, current swimming stroke, current location, current speed, head motions, head accelerations, current head orientation, and current heart rate. This memory device (942) can be part of the integrated circuit (930), but can alternatively be a separate memory device such as a FLASH memory device. This memory device (942) can record reference swimming data that represents the swimming time or times achieved by another swimmer or achieved previously by the user. The recorded reference swimming data can represent swimming times from two or more swimmers that were achieved while the swimmers were swimming the same swimming stroke or different swimming strokes. Therefore, the wearable electronic device (940) can compare the current swimming time or times of the user wearing the wearable electronic device to those in the reference swimming data stored in the electrical memory device (942). The wearable electronic device (940) can also then provide comparison results and feedback to the user using the electrical sound speaker (705) while the user wearing the wearable electronic device (940) is swimming in water.

Similar wearable electronic devices can also be conceived to provide comparison results and feedback to the user using its electrical sound speaker regarding activities performed on land, such as walking, jogging, cycling, vertical jumping, and other physical activities. For example, the recorded reference data can represent the number of steps taken in a day by the same user or a different user. The wearable electronic device could then provide audio feedback in real time that states the difference between the number of steps the user has currently taken and the number of steps taken by the user or users represented in the reference data.

Exemplary procedures for data comparison are illustrated by the flowchart in FIG. 5(i). Using the motion sensor (941), the wearable electronic device (940) can determine the swimming times and swimming stroke of the swimmer. Using the wired (529) or wireless interfaces (949), swimming data from multiple different swimmers can be collected in an external database such as that of a website or a backend of a mobile application. The user of the wearable electronic device (940) can select another swimmer's set of reference swimming data from the database, and store that reference data in the memory device (942) of the wearable electronic device (940). When the user is swimming, the wearable electronic device (940) can generate swimming data pertaining to the user, and compare that generated swimming data to the reference data in real time. These comparisons can be reported to the user while the user is swimming in water. For example, the wearable electronic device (940) can use the electrical sound speaker (705) to indicate the difference in seconds between the user's most recent swimming time, and the corresponding swimming time in the reference data. Some other comparisons can include comparisons between total distance covered, total Calories burned, swimming pace, and so on.

Figure 5J:
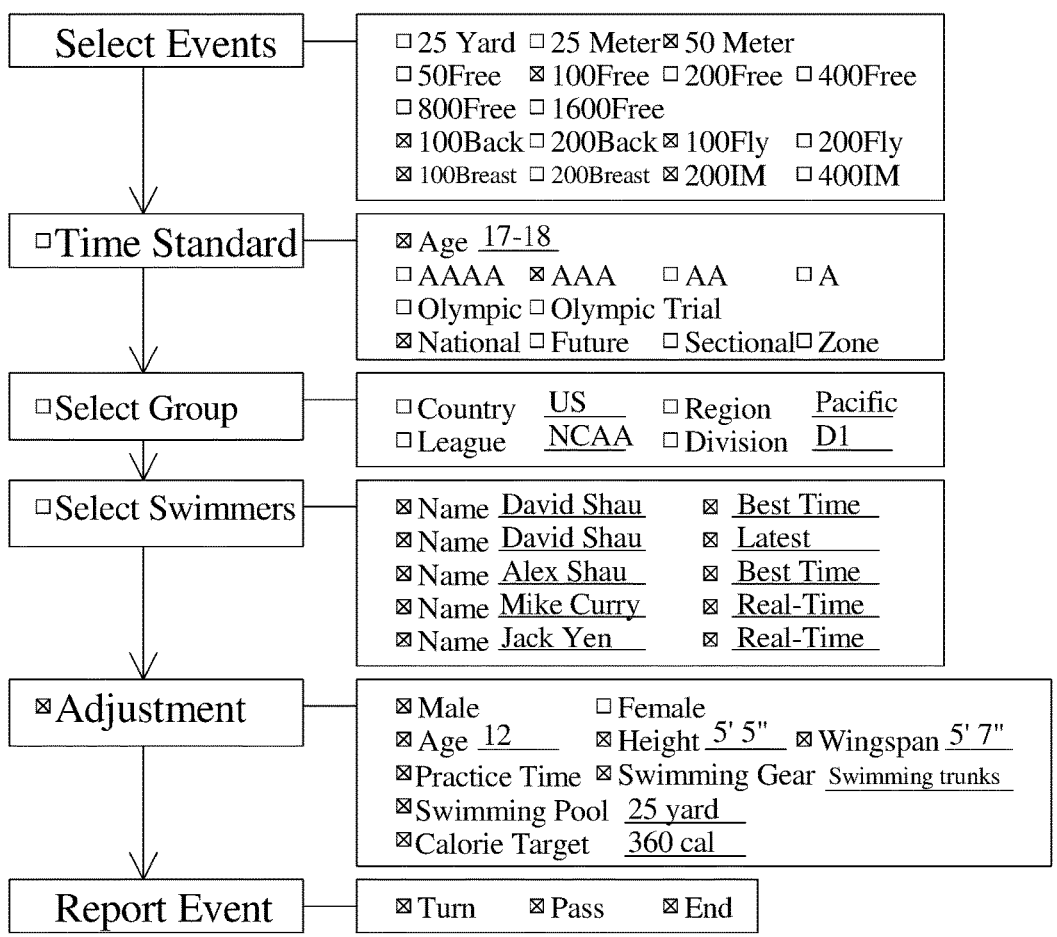
FIG. 5(j) is an exemplary flowchart for various methods for selecting reference swimming data.

FIG. 5(j) is an exemplary flowchart for various methods for filtering and selecting reference data from a large database. For example, a user can select the swimming events for the comparisons such as the 100 meter freestyle, 100 meter backstroke, 100 meter butterfly, 100 meter breaststroke, and 200 meter individual medley, as shown in FIG. 5(j). A user can also select widely accepted swimming time standards as a reference. Swimming time standards are standardized times for certain swimming events that are widely accepted. For example, in 2016, the U.S Olympic Trials swimming time standard for the men's 100 meter freestyle was 50.69 seconds. This means that if a male swimmer swam a 100 meter freestyle in 50.69 seconds or less, they would obtain or achieve the Olympic Trials time standard for the year 2016. It was also nationally recognized and accepted that male swimmers who achieved that time standard could compete in the 100 meter freestyle at the U.S 2016 Olympic Trials. In FIG. 5(j), the user selected the 17-18 age group AAA time standard and the Nationals time standard as reference times. By choosing these swimming events and swimming time standards, the user will be able to swim those events, and receive audio feedback from the electrical sound speaker (705) that can state how close the user is to the selected time standards after the user finishes swimming that event. In addition, the user can receive audio feedback from the electrical sound speaker (705) that indicates how many seconds ahead or behind pace the user is from a selected time standard while the user is swimming the event that corresponds to that time standard. A user can also indicate what population of swimmers he or she would like to be compared to. For example, the user selected to compare his or her swimming performance to swimming times recorded by NCAA division 1 swimmers in the pacific region of United States, as shown in FIG. 5(j). The reference swimming data stored in the wearable electronic device can also represent a specific swimming time of a selected swimmer or a previous swimming time of the user wearing the wearable electronic device. Therefore, a user can indirectly compete with one or many individual swimmers. For example, the user selected to compare his or her swimming time to David Shau's recorded fastest swimming time, David Shau's recorded latest swimming time, and Alex Shau's recorded fastest swimming time. In addition, the user also selected to compete with Mike Curry and Jack Yen in real time, as shown by the example in FIG. 5(j). Using wearable electronic devices (940) equipped with wireless interfaces, it is possible to compare the swimming performance of multiple swimmers while they are all swimming in water, even when they are separated by long distances.

Sometimes it is not practical trying to compete with swimmers who possess unfair advantages over the user. For example, a 12 year old younger brother would not likely be able to achieve similar swimming times of his 25 year old brother. However, a wearable electronic device of the present invention can use the swimming data of the 25 year old brother and account for age difference to generate a set of reference data that represents the relative performance of the older brother at 12 years old. In this way, the younger brother can use a wearable electronic device of the present invention to compete with his older brother on a relative scale instead of a literal scale—as if his older brother were actually 12 years old. Similarly, the reference data can be adjusted for differences in body types. For example, a younger brother who is 5 feet 5 inches tall can fairly compete with a 6 foot 4 inch tall older brother using scaled and adjusted reference data calculated from the swimming results of said older brother. The reference data of the 6 foot 4 inch tall brother would be adjusted and scaled to a dataset that represents the older brother as if he were 5 feet 5 inches tall. Similar adjustments are applicable to differences in wingspan, shoe size, hand size, or other body type differences. Furthermore, this method of relative scaling can also be applied to differences in swimming experiences, or total number of hours spent swimming. For example, a recreational swimmer can compete with a competitive or professional swimming on a similar relative scale as mentioned before. Furthermore, the differences in swimming gear can also be accounted for. For example, reference data recorded by a swimmer wearing a technical suit can be scaled to an equivalent dataset of the same swimmer wearing swim trunks, as shown in the examples in FIG. 5(j). The user can also customize when he or she will receive notifications from the wearable electronic device (940) regarding comparison results. For example, the wearable electronic device (940) can notify the user the time differences relative to swimming times in the reference data after each lap or at the end of a swimming event. The wearable electronic device (940) also can notify the user when the user has passed a swimmer, or in other words covered more distance in the same amount of time, represented by a set of reference data. Similar comparison functions are also applicable to other physical activities such as running, biking, climbing, walking, jumping, and so on.

While specific embodiments of the invention have been illustrated and described herein, it is realized that other modifications and changes will occur to those skilled in the art. It is therefore to be understood that the appended claims are intended to cover all modifications and changes as fall within the true spirit and scope of the invention.

What is claimed is:

1. A wearable electronic device that is designed to be worn on the head of a user comprising:
    an electrical sound speaker;
    a magnetic switch that has a hysteresis input-output relationship in which the magnetic switch is turned on when the magnitude of the magnetic field (Bi) detected by the magnetic switch is greater than a manufacturer defined upper threshold value (BH), the magnetic switch is turned off when the magnitude of the magnetic field (Bi) detected by the magnetic switch is less than a manufacturer defined lower threshold value (BL) where BL is less than BH, the magnetic switch remains on when it is switched on until Bi becomes less than BL, and the magnetic switch remains off when it is switched off until Bi becomes greater than BH; and
    a waterproof package that encloses the magnetic switch, where such waterproof package satisfies the IPX7 water resistance standard, meaning that such waterproof package can remain submerged in one-meter deep water for 30 minutes without enduring damages to the electrical components enclosed by the waterproof package, wherein the wearable electronic device can use the output of the magnetic switch to determine whether to pause or to play the music played by the electrical sound speaker.

2. The magnetic switch of the wearable electronic device in claim 1 comprises a Hall effect magnetic sensor.

3. The wearable electronic device in claim 1 further comprises a plurality of magnetic switches.

4. The wearable electronic device in claim 1 further comprises a magnet.

5. The wearable electronic device in claim 1 can use the output of the magnetic switch of the wearable electronic device to determine whether to increase or to decrease the volume of the music played by the electrical sound speaker.

6. The wearable electronic device in claim 1 can use the output of the magnetic switch of the wearable electronic device to determine whether to skip one music file forward or skip one music file backward for the music played by the electrical sound speaker.

7. The wearable electronic device in claim 1 further comprises a motion sensor that can detect the head orientation of the user relative to the direction of the gravity acceleration vector while the user is swimming in water.

8. The wearable electronic device in claim 7 can determine the swimming strokes that the swimmer wearing the wearable electronic device is swimming using the outputs of the motion sensor of the wearable electronic device.

9. The wearable electronic device in claim 7 can determine the swimming time of the swimmer wearing the wearable electronic device.

10. The wearable electronic device in claim 7 can determine the number of laps the swimmer wearing the wearable electronic device has swum.

11. The wearable electronic device in claim 7 can estimate the number of Calories burned by the swimmer wearing the wearable electronic device.

12. The wearable electronic device in claim 7 can notify the user wearing the wearable electronic device the swimming stroke that the user is swimming using the sound speaker of the wearable electronic device while the swimmer is swimming in water.

13. The wearable electronic device in claim 7 can notify the user wearing the wearable electronic device the swimming time or times of the user by using the sound speaker of the wearable electronic device while the swimmer is swimming in water.

14. The wearable electronic device in claim 7 can notify the user wearing the wearable electronic device the number of laps the user has swum using the sound speaker of the wearable electronic device while the swimmer is swimming in water.

15. The wearable electronic device in claim 7 can notify the user wearing the wearable electronic device the estimated number of Calories burned by the user using the sound speaker of the wearable electronic device while the swimmer is swimming in water.

16. The wearable electronic device in claim 7 can notify the user wearing the wearable electronic device the time difference between the current swimming time of the user and that or those of a swimmer represented by reference swimming data.

17. The waterproof package of the wearable electronic device in claim 1 can remain submerged in three-meter deep water for 30 minutes without enduring damages to the electrical components enclosed by the waterproof package.

18. The waterproof package of the wearable electronic device in claim 1 can sustain a three-meter free fall into water without enduring damages to the electrical components enclosed by the waterproof package.

19. The waterproof package of the wearable electronic device in claim 1 can sustain a three-meter free fall into water, followed by continuous submersion under three-meter deep water for 30 minutes without enduring damages to the electrical components enclosed by the waterproof package.

* * * * *